(12) United States Patent
Li et al.

(10) Patent No.: US 8,563,546 B2
(45) Date of Patent: *Oct. 22, 2013

(54) HETEROCYCLIC NITROGENOUS OR OXYGENOUS COMPOUNDS WITH INSECTICIDAL ACTIVITY FORMED FROM DIALDEHYDES AND THEIR PREPARATION AND USES THEREOF

(75) Inventors: Zhong Li, Shanghai (CN); Xuhong Qian, Shanghai (CN); Xusheng Shao, Shanghai (CN); Xiaoyong Xu, Shanghai (CN); Liming Tao, Shanghai (CN); Gonghua Song, Shanghai (CN)

(73) Assignees: East China University of Science and Technology, Shanghai (CN); Shanghai Shengnong Pesticide Co., Ltd., Shanghai (CN)

( * ) Notice: Subject to any disclaimer, the term of this patent is extended or adjusted under 35 U.S.C. 154(b) by 167 days.

This patent is subject to a terminal disclaimer.

(21) Appl. No.: 13/140,968

(22) PCT Filed: Dec. 18, 2009

(86) PCT No.: PCT/CN2009/075693
§ 371 (c)(1),
(2), (4) Date: Jul. 20, 2011

(87) PCT Pub. No.: WO2010/069266
PCT Pub. Date: Jun. 24, 2010

(65) Prior Publication Data
US 2011/0269751 A1    Nov. 3, 2011

(30) Foreign Application Priority Data
Dec. 19, 2008  (CN) .......................... 2008 1 0207355

(51) Int. Cl.
*A01N 43/90*  (2006.01)
*A01N 43/40*  (2006.01)
*C07D 487/16*  (2006.01)
*C07D 498/18*  (2006.01)

(52) U.S. Cl.
USPC ..................................... 514/230.2; 514/230.5

(58) Field of Classification Search
USPC .......................... 544/90, 95; 514/230.2, 230.5
See application file for complete search history.

(56) References Cited

U.S. PATENT DOCUMENTS

| | | | |
|---|---|---|---|
| 4,742,060 A | 5/1988 | Shiokawa et al. | |
| 4,831,036 A | 5/1989 | Wolf et al. | |
| 4,849,432 A | 7/1989 | Shiokawa et al. | |
| 4,876,263 A | 10/1989 | Shiokawa et al. | |
| 4,914,113 A | 4/1990 | Shiokawa et al. | |

FOREIGN PATENT DOCUMENTS

| | | |
|---|---|---|
| EP | 0 192 060 | 8/1986 |
| EP | 0 235 725 | 9/1987 |
| EP | 0 247 477 | 12/1987 |
| EP | 0 296 453 | 12/1988 |
| EP | 0 315 826 | 5/1989 |
| EP | 0 386 565 | 9/1990 |
| EP | 0 580 553 | 1/1994 |
| EP | 0 685 477 | 12/1995 |
| EP | 1 031 566 | 8/2000 |
| JP | 62-292765 | 12/1987 |
| JP | 7242633 | 9/1995 |
| JP | 8259568 | 10/1996 |
| JP | 8291171 | 11/1996 |
| WO | 2004/056178 | 7/2004 |
| WO | 2006/056108 | 6/2006 |
| WO | 2007/101369 | 9/2007 |
| WO | 2009/094867 | 8/2009 |

OTHER PUBLICATIONS

Noguchi, M. et al., "Chirality transfer in the ene-reactions of 3-{2-(2S)-[2-(substituted)vinyl]pyrrolidin-1-yl}-2-(substituted)acrolein derivatives," Tetrahedron Letters, vol. 41 (2000) p. 8489-8493.

Noguchi, M. et al., "Thermal Ene Reactions of 3-(Alk-2-enyl)benzylamino-2-(methoxycarbonyl)acrolein Derivatives Leading to 4,5-Dihydro-1H-azepines," Tetrahedron, vol. 56 (2000) p. 1299-1307.

Shao, X. et al., "Divalent and Oxabridged Neonicotinoids Constructed by Dialdehydes and Nitromethylene Analogues of Imidacloprid; Design, Synthesis, Crystal Structure, and Insecticidal Activities," Journal of Agricultural and Food Chemistry, vol. 58 (2010), p. 2696-2702.

International Search Report for international application No. PCT/CN2009/075693, dated Mar. 25, 2010 (10 pages).

*Primary Examiner* — Kahsay Habte
(74) *Attorney, Agent, or Firm* — Hamre, Schumann, Mueller & Larson, P.C.

(57) ABSTRACT

The heterocyclic nitrogenous or oxygenous compounds of formula (A), (B), (C) or (D) formed from dialdehydes, their optical isomers, cis- and trans-isomers, or agrochemically acceptable salts, their preparation methods, agrochemical compositions comprising the compounds and the uses thereof are provided. The compounds and their derivatives have high insecticidal activities to several farming and forestry pests including homoptera and lepidoptera pests, such as aphis, fulgorid, whitefly, leafhopper, common thrips, cotton bollworm, cabbage caterpillar, cabbage moth, cotton leafworm, armyworm and so on.

9 Claims, No Drawings

HETEROCYCLIC NITROGENOUS OR OXYGENOUS COMPOUNDS WITH INSECTICIDAL ACTIVITY FORMED FROM DIALDEHYDES AND THEIR PREPARATION AND USES THEREOF

FIELD OF THE INVENTION

This invention relates to novel neonicotinoid derivatives, the preparation method and the uses thereof.

BACKGROUND OF THE INVENTION

Represented by Imidacloprid, neonicotinoid insecticide has been act as a hot area of pesticide discovery, with the character of high insecticidal activity, wide insecticidal spectrum, low toxic to mammals and aquatic animals, good systematic properties, appropriate field stability and environmental friendship. After Imidacloprid, a series of neonicotinoid insecticides such as Thiacloprid, Clothianidin, Thiamethoxam, Acetamiprid, Nitenpyram and Dinotefuran were developed (EP 247477, 296453, 685477, 235725, 235725, 315826, 192060, 244777, 0386565, 580553, 1031566, JP 62292765, 8259568, 8291171 and 7242633).

However, the application and development of these compounds are limited due to the resistance caused by over frequent use of Imidacloprid and cross-resistance among neonicotinoid insecticides caused by structural similarity. Meanwhile, the neonicotinoid insecticides mainly show high activity to Homoptera and Coleoptera pests, and the narrow insecticidal spectrum limits their broad application in pest control.

Therefore, it is urgent in the art to develop compounds with efficient activities from high active nitromethylene compounds so as to solve the problem of resistance, enlarge the insecticidal spectrum and apply them in insecticide compositions.

SUMMARY OF INVENTION

This invention provides novel effective insecticides, which resolve the resistance problem of neonicotinoid insecticides, enlarge the insecticidal spectrum and address the issues existed in the art.

One object of the invention is to provide derivatives for effective pest control and the preparation thereof.

Another object of the invention is to provide the protection for growing and harvested plants and prevent them from the invading of insect.

According to the first aspect of the invention, it is provided a compound of formula (A), (B), (C) or (D), its optical isomer, cis-trans isomer, or its agrochemically acceptable salts thereof

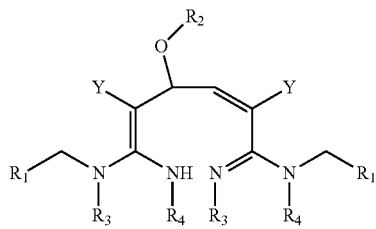

(A)

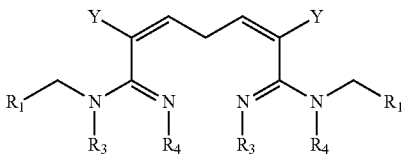

(B)

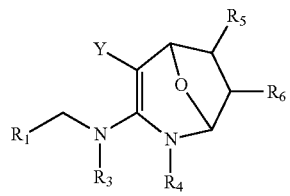

(C)

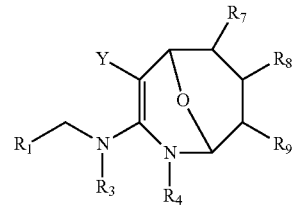

(D)

wherein $R_1$ is 5 or 6 membered heterocycle containing nitrogen, oxygen and/or sulfur atom, halo-substituted 5 or 6 membered heterocycle containing nitrogen, oxygen and/or sulfur atom, substituted or unsubstituted phenyl, wherein the substituents are one or more groups selected from the group consisting of halogen atoms, $C_{1-4}$ halo-alkyl or $C_{1-4}$ chloroalkoxyl;

$R_2$ is H, $C_{1-8}$ saturated or unsaturated alkyl, halo-substituted $C_{1-8}$ saturated or unsaturated alkyl, —$CH_2CH_2OCH_2CH_3$, —$CH_2CH_2OCH_3$, $C_{1-8}$ saturated or unsaturated alkoxyl, phenyl, benzyl, $C_{1-4}$ alkyl-carbonyl, or $C_{1-4}$ alkyl-sulfonyl;

$R_3$ and $R_4$ are independently selected from H, $C_{1-6}$ alkyl, allyl, benzyl, $C_{1-4}$ alkoxyl-$C_{1-4}$ alkyl, $C_{1-4}$ alkoxyl-carbonyl, phenoxycarbonyl, $C_{2-6}$ alkynyl-carbonyl, $C_{2-3}$ alkenyl-carbonyl, $C_{3-6}$ cycloalkyl-carbonyl, unsubstituted benzoyl group or benzoyl group substituted by one or more groups selected from the group consisting of halogen atoms, $C_{1-4}$ alkyl, $C_{1-4}$ halo-alkyl, $C_{1-4}$ alkoxyl or $C_{1-4}$ alkyl-carbonyl, furan carbonyl or N, N-dimethyl carbonyl; or $R_3$ and $R_4$ together form —$CH_2$—$CH_2$—, —$CH_2$—$CH_2$—$CH_2$— or —$CH_2$—XR—$CH_2$—, wherein X represents N, O, S or other heteroatom; R is substituent on X and selected from H, $C_{1-6}$ alkyl, allyl, benzyl, phenyl, $C_{1-4}$ alkoxyl-$C_{1-4}$ alkyl, $C_{1-4}$ alkoxyl-carbonyl, phenoxycarbonyl, $C_{2-6}$ alkynyl-carbonyl, $C_{2-3}$ alkenyl-carbonyl, $C_{3-6}$ cycloalkyl-carbonyl, unsubstitued benzoyl group or benzoyl group substituted by one or more groups selected from the group consisting of halogen atoms, $C_{1-4}$ halo-alkyl, $C_{1-8}$ saturated or unsaturated alkyl or alkoxyl, or $C_{1-4}$ alkyl-carbonyl, furan carbonyl or N, N-dimethyl carbonyl.

$R_5$, $R_6$, $R_7$, $R_8$ and $R_9$ are H, saturated or unsaturated $C_{1-4}$ alkyl, halogen, saturated or unsaturated $C_{1-8}$ alkoxyl, saturated or unsaturated $C_{1-4}$ halo-alkoxyl, $C_{1-4}$ alkyl-carbonyl, $C_{1-8}$ alkyl-ester, $C_{1-4}$ alkyl-sulfonyl, phenyl or benzyl;

Y is nitro, cyano, trifluoromethyl, trifluoroacetyl, or trifluoromethylsulfonyl.

In one embodiment, $R_1$ is selected from pyridyl, thiazolyl, pyrimidinyl, tetrahydrofuryl, oxazolyl, or the halogenated groups thereof.

In one embodiment, the preferable $R_1$ represents halopyridyl, halothiazolyl, halopyrimidinyl, halotetrahydrofuryl, or halooxazolyl. Preferably, the halogenated groups are chlorides.

In another embodiment, $R_1$ represents

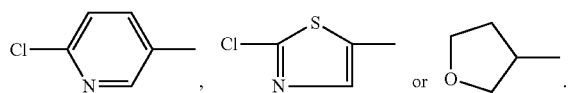

In another embodiment, $R_2$ represents H, saturated or unsaturated $C_{1-4}$ alkyl, saturated or unsaturated $C_{1-4}$ halo-alkyl, $C_{1-4}$ alkyl-carbonyl, unsubstituted benzyl or benzyl substituted by one or more groups selected from the group consisting of halogen atom, $C_{1-4}$ halo-alkyl or $C_{1-4}$ chloro-alkoxyl.

In one embodiment, $R_2$ represents H or $C_{1-3}$ alkyl. More preferably, $R_2$ represents H or methyl.

In another embodiment, $R_3$ and $R_4$ are H, $C_{1-6}$ alkyl, or $R_3$ and $R_4$ together form —$CH_2$—$CH_2$— or —$CH_2$—$CH_2$—$CH_2$—.

In one embodiment, $R_3$ and $R_4$ are hydrogen atom or $C_{1-3}$ alkyl, and preferably H, methyl or ethyl. Alternatively, $R_3$ and $R_4$ together form —$CH_2$—$CH_2$— or —$CH_2$—$CH_2$—$CH_2$—.

In another embodiment, $R_5$, $R_6$, $R_7$, $R_8$ and $R_9$ are H, saturated or unsaturated $C_{1-2}$ alkyl, halogen, saturated or unsaturated $C_{1-4}$ alkoxyl, saturated or unsaturated $C_{1-2}$ halo-alkoxyl, $C_{1-4}$ alkyl-ester group (RCOO—), $C_{1-2}$ alkyl-sulfonyl or trifluoromethanesulfonyl ester group.

In one embodiment, $R_5$, $R_6$, $R_7$, $R_8$ and $R_9$ represent H, methyl, chloride atom, bromide atom, methoxyl or ethoxyl and preferably represent H, methyl and methoxyl.

In another embodiment, Y is nitro group or cyano group.

In one embodiment, Y represents nitro group.

According to the second aspect of the invention, it is provided an agrochemical composition comprising:

(a) 0.001-99.99 wt % of the above-mentioned compound, its optical isomer, cis-trans isomer, agrochemically acceptable salts thereof or the combination thereof; and (b) an agrochemically acceptable carrier or excipient.

In one embodiment, the concentration of component (a) is 0.01-99.9 wt %, and preferably 0.05-90 wt %.

In one embodiment, the agrochemical composition is used to kill or control the insects selected from the group consisting of Coleoptera, Lepidoptera, Hemiptera, Orthoptera, Isoptera and dipteral insects.

In one embodiment, the pests have piercing-sucking type or scratching type mouthparts.

In another embodiment, the pests comprise aphid, planthopper, white fly, leaf hopper, thrips, cotton bollworm, Cabbage caterpillar, Diamondback prodenia litura or army worm.

In another embodiment, the agrochemical composition further comprises other active compounds which are selected from the group consisting of insecticide, cobait, bactericide, acaricide, nematicide, fungicide and growth control agents.

According to the third aspect of the invention, it is provided the use of the agrochemical composition in killing or controlling agricultural pests, sanitary pests and animal health hazard pests; or the agrochemical composition is used as an insecticidal composition for killing or controlling agricultural pests, sanitary pests and animal health hazard pests.

According to the forth aspect of the invention, it is provided a method of for killing or controlling agricultural pests, sanitary pests and animal health hazard pests, wherein the method comprises applying the above agrochemical or insecticidal composition onto plants, their surrounding soil or environment that is attacked or will be attacked by insects.

According to the fifth aspect of the invention, it is provided the use of the compound, its optical isomer or cis-trans isomer, an agrochemically acceptable salts or their composition in preparation of insecticide composition.

According to the sixth aspect of the invention, it is provided a method for preparation of the compound, its optical isomer or cis-trans isomer, or agrochemically acceptable salts, wherein the method comprises the following steps:

In the presence of catalytic acid and at 0-60° C., reacting compound of formula (a) with compound (b), (c) or (d), thereby forming compound (A), (B), (C) or (D), wherein $R_2$ represents H,

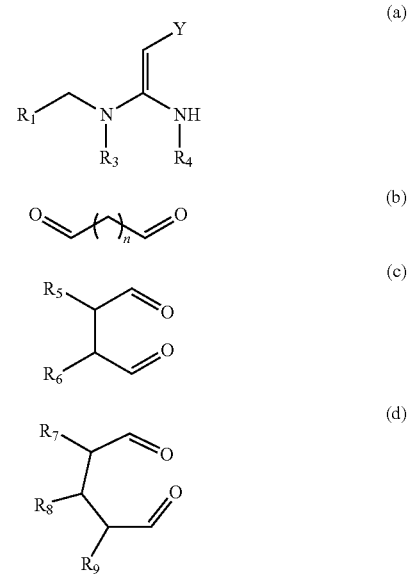

wherein $R_1$, $R_3$, $R_4$, $R_5$, $R_6$, $R_7$, $R_8$, $R_9$ and Y are defined as hereinabove, and n is 0 or 1.

In one embodiment, the reaction temperature is 15-45° C., and preferably 20-30° C.

In another embodiment, the solvent is chosen from acetonitrile or ethanol, and preferably acetonitrile.

In another embodiment, the catalytic acid is chosen from concentrated hydrochloric acid, concentrated sulfuric acid or benzoic acid, and preferably concentrated hydrochloric acid.

In one embodiment, the method comprises:

in the presence of catalytic acid, the following reaction is carried out at 20-30° C. in acetonitrile for 2-24 hours, thereby forming compound (A), wherein $R_2$ is H:

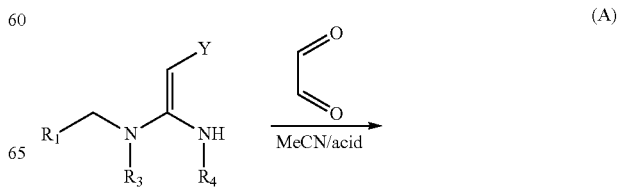

-continued

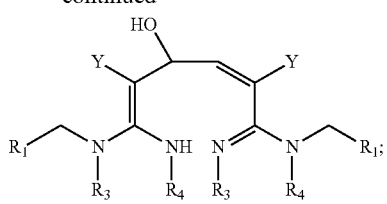

in the presence of catalytic acid, the following reaction is carried out at 20-30° C. in acetonitrile for 2-24 hours, thereby forming compound (B):

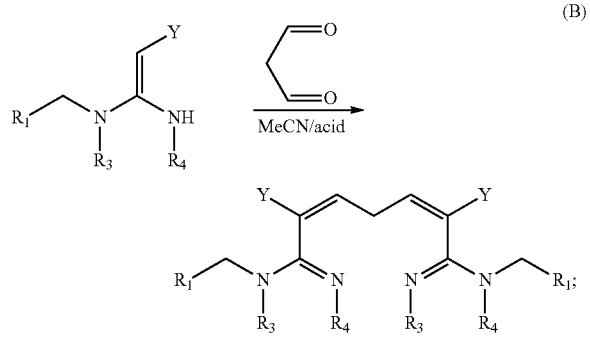

(B)

in the presence of catalytic acid, the following reaction is carried out at 10-50° C. in acetonitrile for 2-24 hours, thereby forming compound (C):

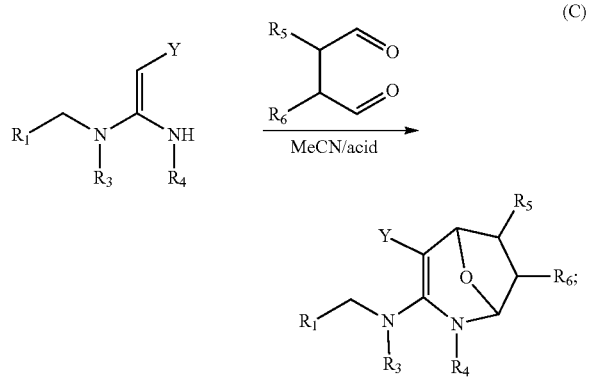

(C)

in the presence of catalytic acid, the following reaction is carried out at 10-50° C. in acetonitrile for 2-24 hours, thereby forming compound (D):

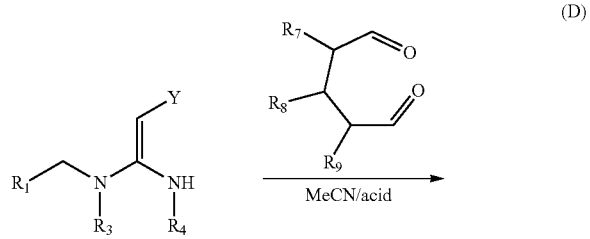

(D)

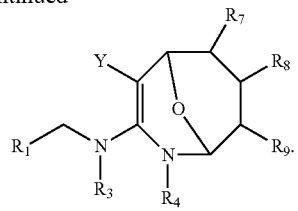

DETAILED DESCRIPTION OF THE INVENTION

After long term and deep investigation, the inventors have synthesized a novel class of neonicotinoid derivatives, which are obtained by the reaction of nitromethylene compounds with dialdehyde based on the nitromethylene group of current nitromethylene neonicotinoid insecticides. The novel derivatives show significantly high activities and enlarged insecticidal spectrum. The inventors completed the present invention based on the above.

Definition of Substitutions

The term "$C_{1-6}$ alkyl" refers to straight or branched alkyl with 1-6 carbon such as methyl, ethyl, propyl, iso-propyl, butyl, iso-butyl, sec-butyl, tent-butyl or some similar groups.

The term "$C_{1-6}$ alkoxyl" refers to straight or branched alkoxyl with 1-6 carbon such as methoxyl, ethoxyl, propoxyl, iso-propoxyl, butoxyl, iso-butoxyl, sec-butoxyl, tert-butoxyl or some similar groups.

The term "halogen" refers to fluorine, chlorine, bromine or iodine. The term "halogenated" refers to one or more substitution with same or different "halogen" as mentioned above, such as trifluoromethyl, pentafluoroethyl or similar groups.

The term "5 or 6 membered heterocyclic alkyl" refers to 5 or 6 membered ring cyclic alkyl containing one or more heteroatoms selected from nitrogen, oxygen or sulfur, such as pyridyl, thiazyl, pyrimidinyl, tetrahydrofuryl, oxazolyl etc.

Preparation of the Compound of Invention

Compounds of the invention can be synthesized as described above. The compound (a) can be obtained according to the technical references in the art, such as WO2006056108A1, WO2007101369A1 and PCT/CN2008/071115.

In one embodiment, compound of formula (A) can be synthesized by the following procedure, wherein is H:

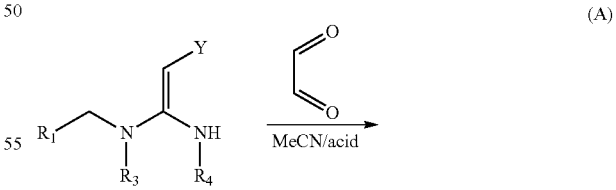

(A)

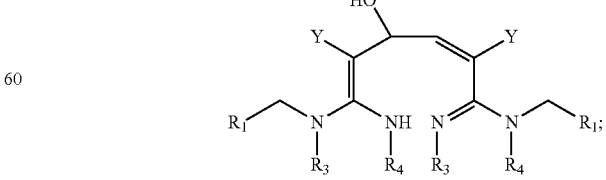

In one embodiment, compound of formula (B) can be synthesized by the following procedure:

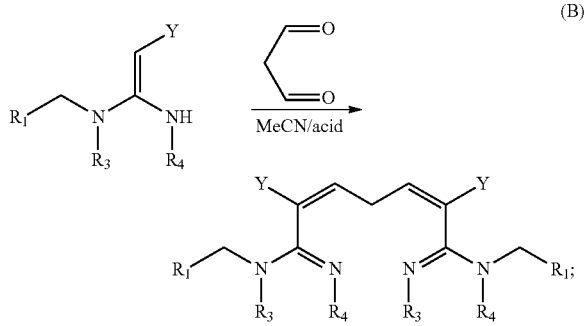

In one embodiment, compound of formula (C) can be synthesized by the following procedure:

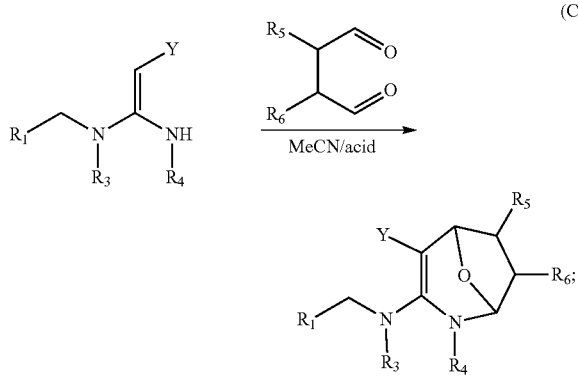

In one embodiment, compound of formula (D) can be synthesized by the following procedure:

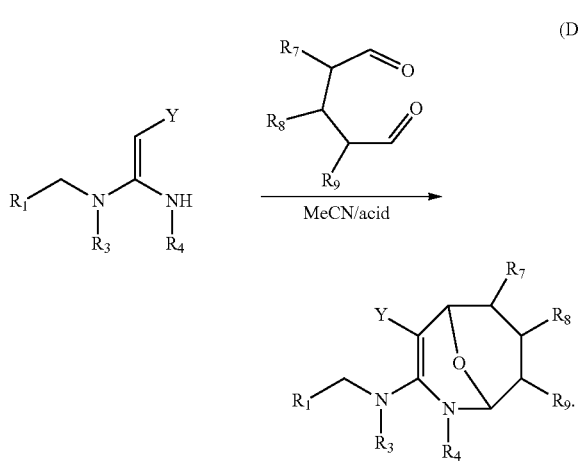

In one embodiment, compound of formula (A) can be synthesized by the following procedure:

(1) A solution of 2-chloro-5-(chloromethyl)pyridine in acetonitrile is added dropwise to 5-10 mole of diamine solution. The reaction is carried out at 0-50° C. for 5-10 hours. After completion, the mixture is distillated under reduced pressure to remove diamine, dissolved in ethyl acetate and evaporated to obtain N-((6-chloropyridin-3-yl)methyl)diamine.

(2) A mixture of N-((6-chloropyridin-3-yl)methyl)diamine and 1,1-dimethylthio-2-nitroethene is dissolved in ethanol and refluxed for 4-8 hours to obtain the nitromethylene compound.

(3) In the presence of acidic catalyst such as hydrochloric acid, sulfuric acid, heteropolyacids etc., nitromethylene compound reacts with oxaldehyde (glyoxal) to obtain compound of formula (A).

In another embodiment, compound of formula (B) can be synthesized by the following procedure:

(1) To a solution of aqueous ethylamine, an appropriate amount of acetonitrile is, added. Then 2-chloro-5-(chloromethyl)pyridine in acetonitrile is added dropwise in ice bath. The reaction is monitored by TLC. After completion, the mixture is added large amount of water, extracted by DCM, dried, filtered and evaporated to obtain N-((6-chloropyridin-3-yl)methyl)ethenamine as oil.

(2) A mixture of N-((6-chloropyridin-3-yl)methyl)ethenamine and 1,1-dimethylthio-2-nitroethene is dissolved in ethanol and refluxed for 4-8 hours. After completion, the mixture is concentrated and purified by column chromatography to obtain N-((6-chloropyridin-3-yl)methyl)-N-ethyl-1-(methylthio)-2-nitroethenamine.

(3) A mixture of methylamine alcohol solution and N-((6-chloropyridin-3-yl)methyl)-N-ethyl-1-(methylthio)-2-nitroethenamine is dissolved in ethanol and reacted for 4-8 hours in ice bath. After completion, the mixture is concentrated and purified by column chromatography to obtain N-((6-chloropyridin-3-yl)methyl)-N-ethyl-N'-methyl-2-nitroethene-1,1-diamine.

(4) In the presence of acidic catalyst such as hydrochloric acid, sulfuric acid, heteropolyacids etc., N-((6-chloropyridin-3-yl)methyl)-N-ethyl-N'-methyl-2-nitroethene-1,1-diamine reacts with malonaldehyde to obtain compound of formula (B).

In another embodiment, compound of formula (C) can be synthesized by the following procedure:

(1) A solution of 2-chloro-5-(chloromethyl)pyridine in acetonitrile is added dropwise to 5-10 mole of diamine solution. The reaction is carried out at 0-50° C. for 5-10 hours. After completion, the mixture is distillated under reduced pressure to remove diamine, dissolved in ethyl acetate and evaporated to obtain N-((6-chloropyridin-3-yl)methyl)diamine.

(2) A mixture of N-((6-chloropyridin-3-yl)methyl)diamine and 1,1-dimethylthio-2-nitroethene is dissolved in ethanol and refluxed for 4-8 hours to obtain the nitromethylene compound.

(3) In the presence of acidic catalyst such as hydrochloric acid, sulfuric acid, heteropolyacids etc., nitromethylene compound reacts with succinaldehyde to obtain compound of formula (C).

In another embodiment, compound of formula (D) can be synthesized by the following procedure:

(1) A solution of 2-chloro-5-(chloromethyl)pyridine in acetonitrile is added dropwise to 5-10 mole of diamine solution. The reaction is carried out at the temperature range of 0-50° C. for 5-10 hours. After completion, the mixture is distillated under reduced pressure to remove diamine, dissolved in ethyl acetate and evaporated to obtain N-((6-chloropyridin-3-yl)methyl)diamine.

(2) A mixture of N-((6-chloropyridin-3-yl)methyl)diamine and 1,1-dimethylthio-2-nitroethene is dissolved in ethanol and refluxed for 4-8 hours to obtain the nitromethylene compound.

(3): In the presence of acidic catalyst such as hydrochloric acid, sulfuric acid, heteropolyacids etc., nitromethylene compound reacts with glutaraldehyde to obtain compound of formula (D).

Insecticidal Activity of Active Compounds of Invention

The terms "active ingredient of the invention" or "active compound of the invention" represent the invented compound, its optical isomer or cis-trans isomer, or an agrochemically acceptable salts thereof. The "active compound of the invention" shows significantly increased activities and broadened insecticidal spectrum.

The term "agrochemically acceptable salts" means that the anion of the salt is known or acceptable when forming the insecticidally acceptable salt. Preferably, the salt is water-soluble. The salts formed by the compounds of formula (A), (B), (C) and (D) include salts formed with inorganic acid (e.g., hydrochlorate, phosphate, sulfate, and nitrate) and salts formed with organic acid (e.g., acetate and benzoate).

The active compound of this invention can be used to control and kill general agriculture and plant insects, storage cereal insects, public health insects and animal health hazard insects. In this invention, term "insecticide" represents any compound that prevents or controls any of the above mentioned insects. The exemplary insects include but are not limited to: Coleoptera: *Sitophilus zeamai, Tribolium castaneum, Henosepilachna vigintioctomaculata, Henosepilachna spars, Agriotes fuscicollis, Anomala cupripes, Popillia quadriguttata, Monolepta hieroglyphica, Monochamus alternatus, Echinocnemus squameus, Basiprionota bisignata, Anoplophora chinensis, Apripona germari, Scolytus schevy, Agriotes fuscicollis*.

Lepidoptera: *Lymantria dispar, Malacosoma neustria testacea, Diaphania perspectalis, Clania variegate, Cnidocampa flauescens, Dendrolimus punctatus, Orgyia gonostigma, Paranthrene tabaniformis, Spodoptera litura, Chilo suppressalis, Ostrinia nubilalis, Ephestia cautella, Adoxophyes orana, Laspyresia splendana, Agrotis fucosa, Galleria mellonella, Plutella xylostella, Phyllocnistis citrella*, or *Mythimna separate*.

Homoptera: *Nephotettix cincticeps, Nilaparvata lugens, Pseudococcus comstocki, Unaspis yanonensis, Myzus persicae, Aphis gossydii, Lipaphis erysimi pseudobrassicae, Stephanitis nashi*, or *Bemisia tabaci*.

Orthoptera: *Blattella germanica, Periplaneta americana, Gryllotalpa africana*, or *Locusta migratoria*.

Isoptera: *Solenopsis invicta, Coptotermes formosanus*.

Diptera: *Musca domestica, Aedes aegypti, Delia platura, Culex* sp., *Anopheles sinensis*.

Animal Health hazard insects: *Boophilus microplus, Haemaphysalis longicornis, Hyalomma anatolicum, Hypoderma* spp., *Fasciola hepatica, Moniezia Blanchard, Ostertagia* spp., *Trypanosoma enansi, Babesia bigemina*, etc.

The compounds of the invention have specific effects on agriculture and plant insects having a piercing-sucking or scratching monthparts, such as aphid, leafhopper, planthopper, thrips, white fly and so on.

Insecticidal Composition Containing Compound of Invention

The invented active compounds can be generally prepared into insecticidal composition. The invented active compounds can be prepared into the conventional formulations, such as solutions, emulsions, suspensions, powders, foams, pastes, granules, aerosols, natural and synthetic materials impregnated with active compounds, and micro-capsules in polymers, the coating complex for seed, preparations used with a combustion device (such as smoking cylindrantherae, smoking can and smoking plate) and ULV cold mist and warm mist preparations.

These formulations may be produced in a known manner, for example, by mixing the active compounds with extenders, which are liquid or liquefied gaseous, solid diluents or carriers, optionally with the use of surface-active agents, which is emulsifying agents and/or dispersing agents, and/or foam-forming agents. In the case of using water as an extender, organic solvents can also be used as auxiliary solvents.

It is generally proper to use liquid solvents as a diluent or carrier, for example, aromatic hydrocarbons, such as xylene, toluene and alkyl naphthalenes; chlorinated aromatic or chlorinated aliphatic hydrocarbons, such as chlorobenzenes, chloroethylenes and methylene chloride; aliphatic hydrocarbons, such as cyclohexane or paraffins, for example, mineral oil fractions; alcohols, such as ethanol or glycol as well as their ethers and esters; ketones, such as acetone, methyl ethyl ketone, methyl isobutyl ketone or cyclohexanone; or uncommon polar solvents, such as dimethylformamide and dimethylsulfoxide, as well as water. By liquefied gaseous diluents or carriers are meant liquids which are gaseous at normal temperature under normal pressure, for example, aerosol propellants, such as halogenated hydrocarbons as well as butane, propane, nitrogen and carbon dioxide.

The solid carrier comprises ground natural minerals, such as kaolins, clays, talcs, quartzs, attapulgites, montmorillonites or kieselguhrs; ground synthetic minerals, such as high dispersed silicic acid, alumina and silicate. The solid carrier used for particles is crushed and fractionated natural rocks such as calcite, marble, pumice, sepiolite and dolomite, as well as synthetic granules of inorganic and organic coarse powder, and granules of organic material such as sawdust, coconut shells, maize cobs and tobacco stalks and the like.

Nonionic and anionic emulsifiers may be used as emulsifying and/or foam-forming agents, such as polyoxyethylene-fatty acid esters, polyoxyethylene-fatty alcohol ethers, for example, alkylaryl polyglycol ethers, alkylsulfonates, alkylsulfates, arylsulfonates as well as albumin hydrolysis products. Dispersing agents include, for example, lignin sulfite waste liquors and methyl cellulose.

Adhesives such as carboxymethyl cellulose and natural and synthetic polymers, (such as gum arabic, polyvinyl alcohol and polyvinyl acetate) in the form of powders, granules or emulsions can be used in the formulations. It is possible to use colorants such as inorganic dyestuffs, for example, iron oxide, cobalt oxide and Prussian Blue, and organic dyestuffs, such as diazo dyestuffs or metal phthalo-cyanine dyestuffs, and trace nutritional agent, such as the salts of iron, manganese, boron, copper, cobalt, aluminum and zinc.

The active compound of the invention can be present as a mixture with other active compounds in a commercial formulation or a use form prepared from the commercial formulation. The other compounds can be insecticide, bactericide, acaricide, nematocide, fungicide, growth controller and the like. The insecticide includes, e.g., phosphates, carbamate, pyrethroids, chlorinated hydrocarbons, benzoylurea, nereistoxin and material produced by microbion such as avermectin.

Furthermore, the active compound of the invention can be present as a mixture with a synergist in a commercial formulation or a use form prepared from the commercial formulation. Synergist is used to enhance the action of active compound, as the compound itself is active it is optional to use the synergist.

Generally, the formulations contain 0.001-99.99 wt %, preferably 0.01-99.9 wt %, and more preferably 0.05-90 wt % of the active compound of invention. The concentration of the active compound in the use form prepared from the commercial formulation can vary within a wide range. The active compound concentration of the formulation for use is, for example, 0.0000001-100% (g/v), and preferably 0.0001-1%.

EXAMPLES

The invention is further illustrated by the following examples. It should be appreciated that these examples are only intended to illustrate the invention, but not to limit the scope of the invention. For the experimental methods in the following examples, they are performed under routine conditions, or as instructed by the manufacturers, unless otherwise specified. The percentage and parts are calculated by weight. Term "r.t." represents room temperature.

Example 1

Synthesis of 4-(1-((6-chloropyridin-3-yl)methyl)-4,5-dihydro-1H-imidazol-2-yl)-1-(1-((6-chloropyridin-3-yl)methyl)imidazolidin-2-ylidene)-1,4-dinitrobut-3-en-2-ol (Compound 13)

According to the method described in WO 2006056108A1 and WO2007101369A1, 2-chloro-5-((2-(nitromethylene)imidazolidin-1-yl)methyl)pyridine was prepared from 2-chloro-5-(chloromethyl)pyridine (0.03 mol) with 56% yield. Rf=0.46 (petroleum ether:EtOAc=1:1); mp=156.9° C.-161.8° C.; GC MS (m/s): 220 (25), 126(100), 90 (9).

Synthesis of 4-(1-((6-chloropyridin-3-yl)methyl)-4,5-dihydro-1H-imidazol-2-yl)-1-(1-((6-chloropyridin-3-yl)methyl)imidazolidin-2-ylidene)-1,4-dinitrobut-3-en-2-ol

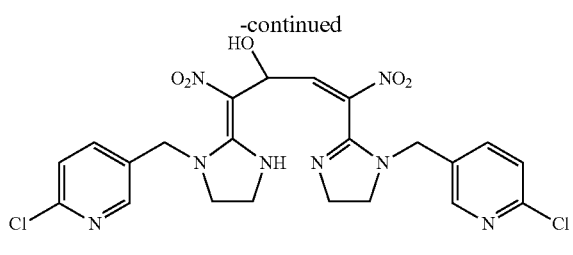

To a 50 ml round bottom flask was added 1.27 g (0.005 mol) 2-chloro-5-((2-(nitromethylene)imidazolidin-1-yl)methyl)pyridine, 30 ml acetonitrile and 3 ml 30% oxaldehyde aqueous solution. After stirring for 0.5 hour, catalytic concentrated HCl was added. The reaction was then stirred and monitored by TLC until completion. The mixture was filtered afterwards to afford white powder, which was crystallized to give 1.05 g pure final product as white powder solid. Yield: about 76%.

mp=164.6-165.3° C.; $^1$H NMR (400 Mz, DMSO-$d_6$): δ 9.01 (s, 1H), 8.41 (d, J=2.0 Hz, 1H), 8.38 (d, J=2.0 Hz, 1H), 7.80-7.86 (m, 2H), 7.51-7.54 (m, 2H), 6.50 (d, J=7.2 Hz, 1H), 5.34 (d, J=15.2 Hz, 1H), 5.18 (d, J=15.2 Hz, 1H), 4.84 (dd, $J_1$=2.4 Hz, $J_2$=7.2 Hz, 1H), 4.77 (d, J=16.8 Hz, 1H), 4.67 (d, J=16.8 Hz, 1H), 3.98 (d, J=2.4 Hz, 1H), 3.86-3.95 (m, 2H), 3.61-3.80 (m, 5H), 3.40-3.47 (m, 1H) ppm; $^{13}$C NMR (100 Mz, DMSO-$d_6$): δ 162.7, 158.7, 148.3, 148.2, 148.0, 147.7, 138.1, 137.7, 130.9, 130.2, 123.1, 123.0, 102.5, 101.4, 81.4, 53.8, 52.6, 49.4, 48.8, 46.4, 41.2, 41.0 ppm; HRMS (ES+) calcd for $C_{22}H_{23}N_8O_5{}^{35}Cl_2$ (M+H)$^+$, 549.1168. Found, 549.1178. calcd for $C_{22}H_{23}N_8O_5{}^{35}Cl^{37}Cl$ (M+H)$^+$, 551.1139. Found, 551.1152. calcd for $C_{22}H_{23}N_8O_5{}^{37}Cl_2$ (M+H)$^+$, 553.1109. Found, 553.1108.

Example 2

Synthesis of 2-chloro-5-((4-(1-((6-chloropyridin-3-yl)methyl)imidazolidin-2-ylidene)-2-methoxy-1,4-dinitrobut-3-enyl)-4,5-dihydroimidazol-1-yl)methyl)pyridine (Compound 14)

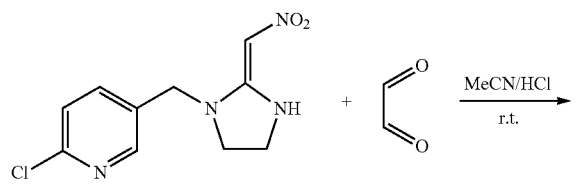

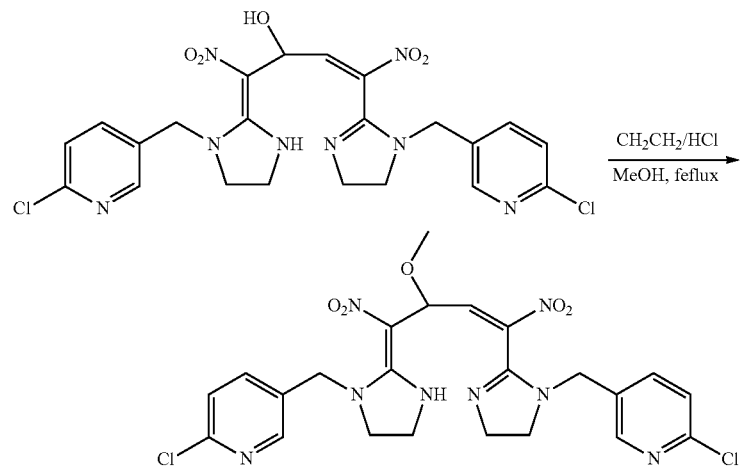

To a 50 ml round bottom flask was added 0.549 g (0.001 mol) compound 13, 10 ml methanol, 50 ml dichloromethane and catalytic concentrated HCl. The reaction was refluxed and monitored by TLC. After completion, the mixture was evaporated to remove solvent and purified by column chromatography to afford final product as yellow powder (62% yield).

mp=151.6-153.1° C.; $^1$H NMR (400 Mz, DMSO-$d_6$): δ 9.03 (s, 1H), 8.38 (d, J=2.0 Hz, 1H), 8.36 (d, J=2.0 Hz, 1H), 7.81-7.85 (m, 2H), 7.49-7.51 (m, 2H), 6.50 (d, J=7.2 Hz, 1H), 5.35 (d, J=15.2 Hz, 1H), 5.19 (d, J=15.2 Hz, 1H), 4.80 (d, $J_1$=7.2 Hz, 1H), 4.77 (d, J=16.8 Hz, 1H), 4.69 (d, J=16.8 Hz, 1H), 3.68 (s, 3H), 3.88-3.95 (m, 2H), 3.61-3.85 (m, 5H), 3.38-3.41 (m, 1H) ppm; $^{13}$C NMR (100 Mz, DMSO-$d_6$): δ 162.6, 158.7, 148.9, 148.3, 148.1, 147.6, 138.1, 137.8, 130.9, 129.9, 122.8, 123.1, 102.2, 101.6, 81.6, 58.7, 53.8, 52.6, 49.6, 48.9, 46.4, 41.3, 41.0 ppm; HRMS (ES+) calcd for $C_{23}H_{25}N_8O_5{}^{35}Cl_2$ (M+H)$^+$, 563.1325. Found, 563.1311. calcd for $C_{23}H_{25}N_8O_5{}^{35}Cl^{37}Cl$ (M+H)$^+$, 565.1295.

Example 3

Synthesis of $N^1,N^7$-bis((6-chloropyridin-3-yl)methyl)-$N^1,N^7$-diethyl-$N^{1'},N^{7'}$-dimethyl-2,6-dinitro-hepta-2,5-dienediamidine (Compound 37)

(1): Synthesis of N-((6-chloropyridin-3-yl)methyl)ethanamine

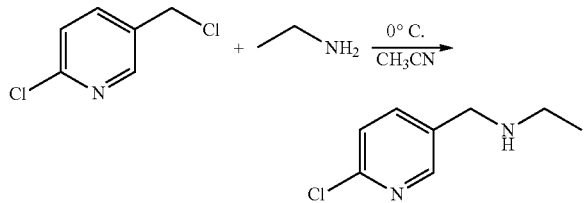

65-70% ethylamine solution (70 g, 1 mol), acetonitrile 50 mL were added into a three necked round bottom flask mounted with pressure-equalizing dropping funnel and thermometer. The solution was stirred in ice bath for 15 min to control the temperature near 0° C. Then, 2-chloro-5-(chloromethyl)pyridine (16.10 g, 0.10 mol) in 25 ml acetonitrile was added by pressure-equalizing dropping funnel in 3.5 hrs with a speed of 3 drop/min. After completion, water was added and the reaction mixture was extracted with DCM. The organic phase was collected, thereby obtaining 14 g N-((6-chloropyridin-3-yl)methyl)ethanamine as oil with 70% yield. GC-MS: m/z (%)=170 ([M]+, 20), 155 (80), 126 (100), 114 (10), 90 (12).

(2): Synthesis of N-((6-chloropyridin-3-yl)methyl)-N-ethyl-1-(methylthio)-2-nitroethenamine To a 100 ml three necked round bottom flask was added N-((6-chloropyridin-3-yl)methyl)ethanamine (17.0 g, 0.1 mol), (2-nitroethene-1,1-diyl)bis(methylsulfane) (15.0 g, 0.09 mol), dry ethanol (50 mL). The mixture was refluxed. After completion, the reaction mixture was cooled to r.t. and concentrated under reduced pressure to obtain crude product as oil, which was purified by column chromatography to afford 5.3 g N-((6-chloropyridin-3-yl)methyl)-N-ethyl-1-(methylthio)-2-nitroethenamine in 18.5% yield.

GC-MS: m/z (%)=242 ([M]+–46, 53), 227 (15), 213 (100), 169 (45), 155 (28), 141 (29), 126 (91), 90 (12).

(3): Synthesis of N-((6-chloropyridin-3-yl)methyl)-N-ethyl-N'-methyl-2-nitroethene-1,1-diamine

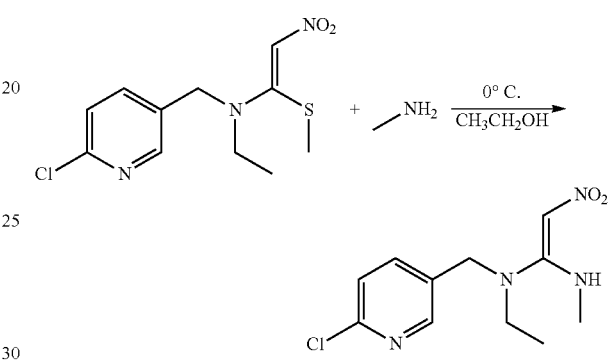

To a 100 ml round bottom flask was added N-((6-chloropyridin-3-yl)methyl)-N-ethyl-1-(methylthio)-2-nitroethenamine (5 g, 0.017 mol), Methylamine alcohol solution (1.8 g, 0.017 mol), dry ethanol (30 mL). The mixture was stirred in ice bath to lower the temperature to 0° C. and continuously stirred until completion. The reaction mixture was evaporated under reduced pressure to remove solvent and concentrated to obtain the syrup which was solved in some DCM and purified by column chromatography using DCM/MeOH=25:1 as eluent and silica as filler. 0.9 g N-((6-chloropyridin-3-yl)methyl)-N-ethyl-N-methyl-2-nitroethene-1,1-diamine was obtained with 19.1% yield. Rf=0.23 (DCM/Acetone=5:1); mp=78-80° C., (lit[67] 79-81° C.); GC-MS: m/z (%)=236 ([M]+–34, 32), 207 (49), 169 (52), 126 (49), 110 (20), 90 (16), 67 (100). 16.65.

(4): Synthesis of $N^1,N^7$-bis((6-chloropyridin-3-yl)methyl)-$N^1,N^7$-diethyl-$N^{1'},N^{7'}$-dimethyl-2,6-dinitro-hepta-2,5-dienediamidine (compound 37)

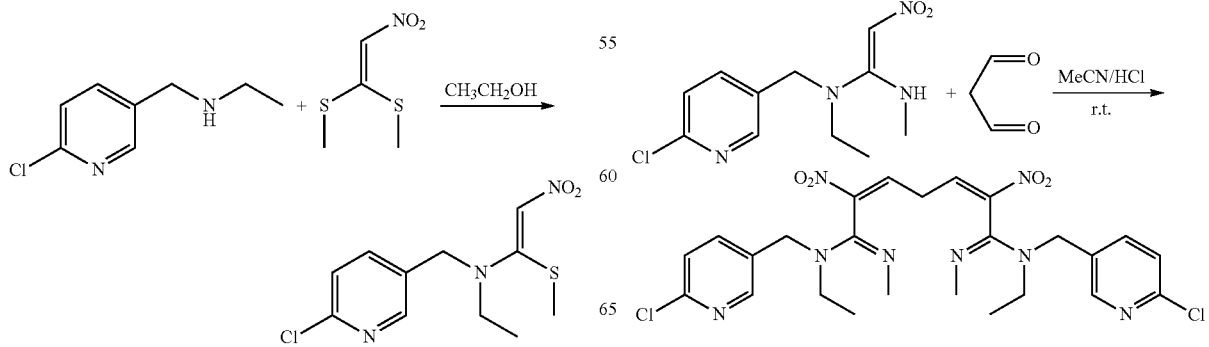

To a 50 ml round bottom flask was added 1.35 g (0.005 mol) N-((6-chloropyridin-3-yl)methyl)-N-ethyl-N-methyl-2-nitroethene-1,1-diamine, 30 ml dry acetonitrile, 0.72 g (0.01 mol) malonaldehyde and catalytic concentrated HCl. The reaction was stirred at r.t. and monitored by TLC. After completion, the mixture was evaporated to remove solvent and purified by column chromatography to afford final product as faint yellow powder with 56% yield.

mp=117.3–118.7° C.; $^1$H NMR (400 Mz, DMSO-$d_6$): δ 8.36 (d, J=2.4 Hz, 2H), 7.88 (dd, $J_1$=2.4 Hz, $J_2$=8.4 Hz, 2H), 7.51 (d, J=8.4 Hz, 2H), 4.97 (t, J=2.8 Hz, 2H), 4.86 (d, J=15.2 Hz, 2H), 4.49 (d, J=15.2 Hz, 2H), 3.95-3.99 (m, 4H), 3.66-3.78 (m, 6H), 3.12-3.21 (m, 2H), 1.91-1.93 (m, 6H) ppm; $^{13}$C NMR (100 Mz, DMSO-$d_6$): δ 156.3, 148.5, 148.1, 137.3, 131.9, 122.5, 104.8, 49.2, 48.9, 48.0, 48.5, 28.1, 20.2 ppm; HRMS (EI+) calcd for $C_{25}H_{30}N_8O_4{}^{35}Cl_2$ (M+), 576.1767. Found, 576.1751.

Example 4

Synthesis of 2-chloro-5-((5-(1-(((6-chloropyridin-3-yl)methyl)-4,5-dihydro-1H-imidazol-2-yl)-1,5-dinitropenta-1,4-dienyl)-4,5-dihydroimidazol-1-yl)methyl)pyridine (Compound 39)

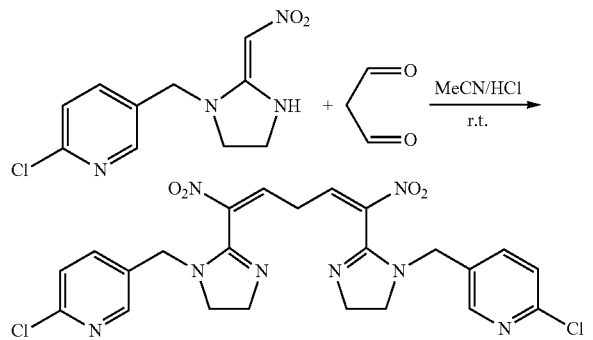

To a 50 ml round bottom flask was added 1.27 g (0.005 mol) 2-chloro-5-((2-(nitromethylene)imidazolidin-1-yl)methyl)pyridine, 30 ml dry acetonitrile, 0.720 g (0.01 mol) malonaldehyde and catalytic concentrated HCl. The reaction was stirred at r.t. and monitored by TLC. After completion, the mixture was evaporated to remove solvent and purified by column chromatography to afford final product as faint yellow powder with 52% yield.

mp=136.5-137.8° C.; $^1$H NMR (400 Mz, DMSO-$d_6$): δ 8.34 (d, J=2.4 Hz, 2H), 7.82 (dd, =2.4 Hz, $J_2$=8.4 Hz, 2H), 7.47 (d, J=8.4 Hz, 2H), 4.96 (t, J=2.8 Hz, 2H), 4.81 (d, J=15.8 Hz, 2H), 4.44 (d, J=15.8 Hz, 2H), 3.92-3.97 (m, 4H), 3.65-3.72 (m, 2H), 3.49-3.56 (m, 2H), 1.92-1.93 (m, 2H) ppm; $^{13}$C NMR (100 Mz, DMSO-$d_6$): δ 155.3, 147.9, 147.8, 138.0, 130.9, 122.7, 104.8, 50.2, 48.9, 48.5, 48.5, 28.1 ppm; HRMS (ES+) calcd for $C_{23}H_{23}N_8O_4{}^{35}Cl_2$ (M+H)$^+$, 545.1219. Found, 545.1201. calcd for $C_{23}H_{23}N_8O_4{}^{35}Cl^{37}Cl$ (M+H)$^+$, 547.1190. Found, 547.1178. calcd for $C_{23}H_{23}N_8O_4{}^{37}Cl_2$ (M+H)$^+$, 549.1160. Found, 549.118.

Example 5

Synthesis of 1-((2-chlorothiazol-5-yl)methyl)-5-(1-((2-chlorothiazol-5-yl) methyl)-4,5-dihydro-1H-imidazol-2-yl)-1,5-dinitropenta-1,4-dienyl)-4,5-dihydro-1H-imidazole (Compound 41)

Following the method described in Example 1, 0.03 mol 2-chloro-5-(chloromethyl)thiazole instead of 2-chloro-5-(chloromethyl)pyridine was used as staring material and 1-((2-chlorothiazol-5-yl)methyl)-2-(nitromethylene)imidazolidine was obtained with 56% yield. GC MS (m/s) 226(24), 132(100), 77 (9).

Synthesis of 1-((2-chlorothiazol-5-yl)methyl)-5-(1-((2-chlorothiazol-5-yl) methyl)-4,5-dihydro-1H-imidazol-2-yl)-1,5-dinitropenta-1,4-dienyl)-4,5-dihydro-1H-imidazole

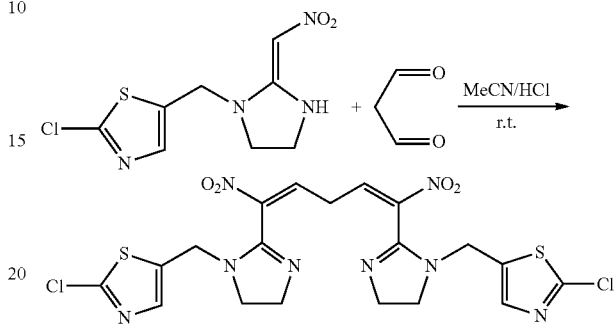

To a 50 ml round bottom flask was added 1.30 g (0.005 mol) 1-((2-chlorothiazol-5-yl)methyl)-2-(nitromethylene) imidazolidine, 30 ml dry acetonitrile, 0.720 g (0.01 mol) malonaldehyde and catalytic concentrated HCl. The reaction was stirred at r.t. and monitored by TLC. After completion, the mixture was evaporated to remove solvent and purified by column chromatography to afford final product as faint yellow powder with 44% yield.

mp=138.6-139.9° C.; $^1$H NMR (400 Mz, DMSO-$d_6$): δ 7.63 (s, 1H), 4.98 (t, J=2.8 Hz, 2H), 4.85 (d, J=15.8 Hz, 2H), 4.43 (d, J=15.8 Hz, 2H), 3.96-3.99 (m, 4H), 3.67-3.71 (m, 2H), 3.51-3.56 (m, 2H), 1.95-1.97 (m, 2H) ppm; $^{13}$C NMR (100 Mz, DMSO-$d_6$): δ 157.6, 149.3, 138.3, 105.8, 50.6, 48.9, 48.4, 48.1, 29.1 ppm; HRMS (ES+) calcd for $C_{19}H_{19}N_8O_4S_2{}^{35}Cl_2$ (M+H)$^+$, 557.0348. Found, 557.0363. calcd for $C_{19}H_{19}N_8O_4S_2{}^{35}Cl^{37}Cl$ (M+H)$^+$, 559.0318. Found, 559.0620.

Example 6

Synthesis of 1-((6-chloropyridin-3-yl)methyl)-5-(1-((6-chloropyridin-3-yl) methyl)-1,4,5,6-tetrahydropyrimidin-2-yl)-1,5-dinitropenta-1,4-dienyl)-1,4,5,6-tetrahydropyrimidine (Compound 43)

According to the method described in WO 2006056108A1 and WO2007101369A1, 1-((6-chloropyridin-3-yl)methyl)-2-(nitromethylene)-hexahydropyrimidine was prepared from 2.42 g (0.015 mmol) 2-chloro-5-(chloromethyl)pyridine with 56% yield; $R_f$=0.19 (EtOH:DCM=1:1); mp=175.7° C.-182.6° C.; GC MS (m/s): 225(100), 196(9), 154(10), 139 (11), 126(31), 113(10), 90 (31).

Synthesis of 1-((6-chloropyridin-3-yl)methyl)-5-(1-((6-chloropyridin-3-yl) methyl)-1,4,5,6-tetrahydropyrimidin-2-yl)-1,5-dinitropenta-1,4-dienyl)-1,4,5,6-tetrahydropyrimidine

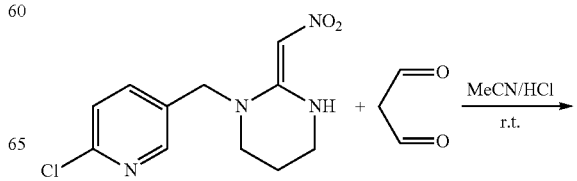

-continued

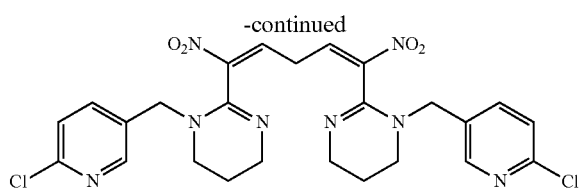

To a 50 ml round bottom flask was added 1.34 g (0.005 mol) 1-((6-chloropyridin-3-yl)methyl)-2-(nitromethylene)-hexahydropyrimidine, 30 ml dry acetonitrile and 0.720 g (0.0 mol) malonaldehyde and catalytic concentrated HCl. The reaction was stirred at r.t. and monitored by TLC. After completion, the mixture was evaporated to remove solvent and purified by column chromatography to afford final product as faint yellow powder with 55% yield.

mp=133.7-134.9° C.; $^1$H NMR (400 Mz, DMSO-$d_6$): δ 8.32 (d, J=2.4 Hz, 2H), 7.81 (dd, $J_1$=2.4 Hz, $J_2$=8.4 Hz, 2H), 7.49 (d, J=8.4 Hz, 2H), 4.93 (t, J=2.8 Hz, 2H), 4.78 (d, J=15.8 Hz, 2H), 4.40 (d, J=15.8 Hz, 2H), 3.91-3.96 (m, 4H), 3.63-3.71 (m, 2H), 3.49-3.53 (m, 2H), 2.32-2.37 (m, 2H), 1.92-1.93 (m, 2H) ppm; $^{13}$C NMR (100 Mz, DMSO-$d_6$): δ 155.6, 148.3, 147.9, 138.0, 130.7, 122.7, 105.1, 50.2, 48.8, 48.5, 48.1, 36.2, 28.0 ppm; HRMS (ES+) calcd for $C_{25}H_{27}N_8O_4{}^{35}Cl_2$ (M+H)$^+$, 572.1454. Found, 572.1468. calcd for $C_{25}H_{27}N_8O_4{}^{35}Cl^{37}Cl$ (M+H)$^+$, 574.1425. Found, 574.1416.

Example 7

Synthesis of N-((6-chloropyridin-3-yl)methyl)-N-ethyl-2-methyl-4-nitro-8-oxa-2-aza-bicyclo[3.2.1]oct-3-en-3-amine (Compound 46)

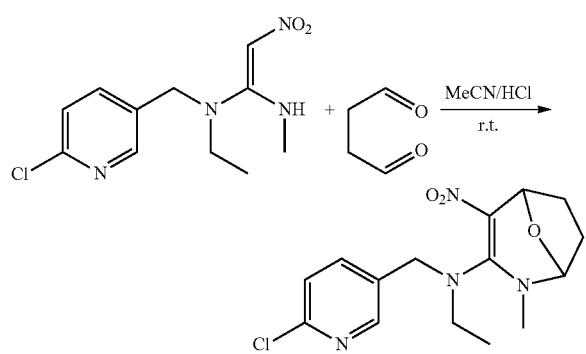

To a 50 ml round bottom flask was added 1.35 g (0.005 mol) N-((6-chloropyridin-3-yl)methyl)-N-ethyl-N'-methyl-2-nitroethene-1,1-diamine, 30 ml dry acetonitrile, 0.860 g (0.01 mol) succinaldehyde and catalytic concentrated HCl. The reaction was stirred at r.t. and monitored by TLC. After completion, the mixture was evaporated to remove solvent and purified by column chromatography to afford final product as faint yellow powder with 40% yield.

mp=125.3-125.7° C.; $^1$H NMR (400 Mz, DMSO-$d_6$): δ 8.72 (s, 1H), 8.27 (d, J=2.4 Hz, 1H), 7.75 (dd, $J_1$=2.4 Hz, $J_2$=8.4 Hz, 1H), 7.58 (d, J=8.4 Hz, 1H), 5.25-5.30 (s, 2H), 4.41-4.50 (m, 2H), 2.96-3.26 (m, 2H), 2.86 (s, 3H), 2.36-2.41 (m, 2H), 1.81-1.5 (m, 4H), 1.16-1.26 (m, 3H) ppm; $^{13}$C NMR (100 Mz, DMSO-d6): δ 158.5, 154.4, 151.6, 150.8, 148.1, 139.3, 137.1, 107.8, 89.5, 65.8, 49.8, 46.9, 40.6, 21.9, 20.3 ppm; HRMS (EI+) calcd for $C_{15}H_{21}N_4O_3{}^{35}Cl$ (M$^+$), 339.1224. Found, 339.1257. calcd for $C_{15}H_{21}N_4O_3{}^{37}Cl$ (M), 341.1194. Found, 341.1213.

Example 8

Synthesis of 1-((6-chloropyridin-3-yl)methyl)-9-nitro-2,3,5,6,7,8-hexahydro-1H-5,8-epoxyimidazo[1,2-a]azepine (Compound 52)

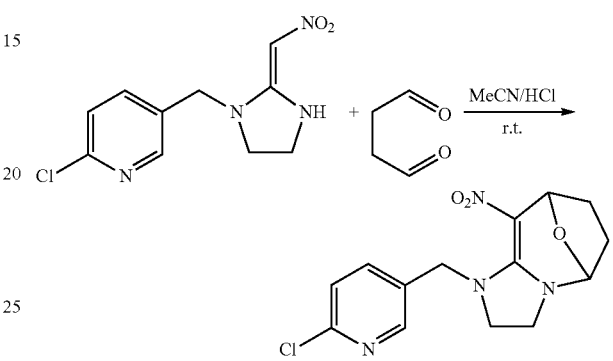

To a 50 ml round bottom flask was added 1.27 g (0.005 mol) 2-chloro-5-((2-(nitromethylene)imidazolidin-1-yl)methyl)pyridine, 30 ml dry acetonitrile, 0.860 g (0.01 mol) succinaldehyde and catalytic concentrated HCl. The reaction was stirred at r.t. and monitored by TLC. After completion, the mixture was evaporated to remove solvent and purified by column chromatography to afford final product as faint yellow powder with 71% yield.

mp=149.0-150.0° C.; $^1$H NMR (400 Mz, DMSO-$d_6$): δ 8.35 (d, J=2.4 Hz, 1H), 7.81 (dd, $J_1$=2.4 Hz, $J_2$=8.4 Hz, 1H), 7.51 (d, J=8.4 Hz, 1H), 5.36-5.39 (s, 2H), 5.00 (d, J=15.6 Hz, 1H), 4.68 (d, J=15.6 Hz, 1H), 3.57-3.73 (m, 4H), 1.94-2.04 (m, 4H) ppm; $^{13}$C NMR (100 Mz, DMSO-$d_6$): δ 155.6, 149.7, 149.6, 139.7, 132.6, 124.5, 109.6, 87.0, 75.1, 51.2, 50.3, 46.6, 31.9, 31.7 ppm; HRMS (ES+) calcd for $C_{14}H_{16}N_4O_3{}^{35}Cl$ (M+H)$^+$, 323.0911. Found, 323.0912. calcd for $C_{14}H_{16}N_4O_3{}^{37}Cl$ (M+H)$^+$, 325.0811. Found, 325.0895. calcd for $C_{14}H_{15}N_4O_3{}^{35}ClNa$ (M+Na)$^+$, 345.0730. Found, 345.0722. calcd for $C_{14}H_{15}N_4O_3{}^{37}ClNa$ (M+Na)$^{++}$, 347.0701. Found, 347.0692.

Example 9

Synthesis of 1-((2-chlorothiazol-5-yl)methyl)-9-nitro-2,3,5,6,7,8-hexahydro-1H-5,8-epoxyimidazo[1,2-a]azepine (Compound 53)

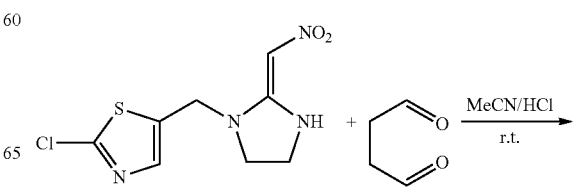

-continued

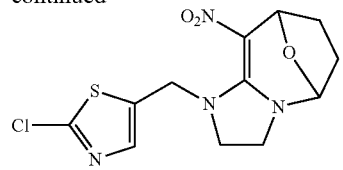

To a 50 ml round bottom flask was added 1.30 g (0.005 mol) 1-((2-chlorothiazol-5-yl)methyl)-2-(nitromethylene)imidazolidine, 30 ml dry acetonitrile, 0.860 g (0.01 mol) succinaldehyde and catalytic concentrated HCl. The reaction was stirred at r.t. and monitored by TLC. After completion, the mixture was evaporated to remove solvent and purified by column chromatography to afford final product as faint yellow powder with 63% yield.

mp=151.7-152.1° C.; $^1$H NMR (400 Mz, DMSO-$d_6$): δ 7.65 (s, 1H), 5.33-5.37 (s, 2H), 5.01 (d, J=15.6 Hz, 1H), 4.69 (d, J=15.6 Hz, 1H), 3.52-3.70 (m, 4H), 1.90-2.01 (m, 4H) ppm; $^{13}$C NMR (100 Mz, DMSO-$d_6$): δ 155.2, 149.6, 139.1, 124.5, 110.6, 87.1, 75.6, 51.3, 50.6, 46.9, 31.9, 31.2 ppm; HMS (ES+) calcd for $C_{12}H_{15}N_4O_3S^{35}Cl$ (M+H)$^+$, 329.0475. Found, 329.0412. calcd for $C_{12}H_{15}N_4O_3S^{37}Cl$ (M+H)$^+$, 331.0446. Found, 331.0423.

Example 10

Synthesis of 1-((6-chloropyridin-3-yl)methyl)-10-nitro-1,2,3,4,6,7,8,9-octahydro-6,9-epoxypyrimido[1,2-a]azepine (Compound 61)

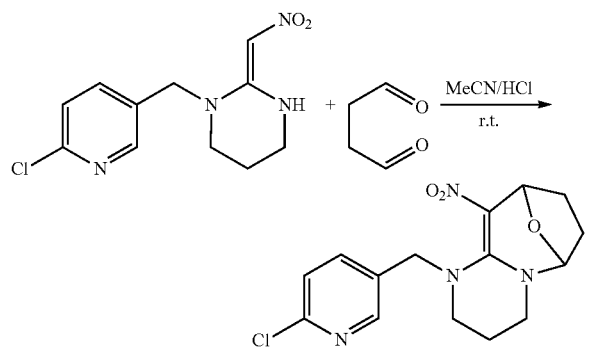

To a 50 ml round bottom flask was added 1.34 g (0.005 mol) (E)-1-((6-chloropyridin-3-yl)methyl)-2-(nitromethylene)-hexahydropyrimidine, 30 ml dry acetonitrile and 0.860 g (0.01 mol) succinaldehyde and catalytic concentrated Hl. The reaction was stirred at r.t. and monitored by TLC. After completion, the mixture was evaporated to remove solvent and purified by column chromatography to afford final product as faint yellow powder with 38% yield.

mp=143.2-144.9° C.; $^1$H NMR (400 Mz, DMSO-$d_6$): δ 8.33 (d, J=2.4 Hz, 1H), 7.80 (dd, $J_1$=2.4 Hz, $J_2$=8.4 Hz, 1H), 7.49 (d, J=8.4 Hz, 1H), 5.32-5.35 (s, 2H), 5.00 (d, J=15.6 Hz, 1H), 4.66 (d, J=15.6 Hz, 1H), 3.51-3.68 (m, 4H), 2.33-2.41 (m, 2H), 1.89-2.00 (m, 4H) ppm; $^{13}$C NMR (100 Mz, DMSO-$d_6$): δ 155.5, 149.6, 149.3, 139.7, 132.6, 124.1, 109.3, 86.6, 75.1, 51.2, 50.7, 46.6, 32.1, 31.7, 26.9 ppm; HRMS (ES+) calcd for $C_{15}H_{19}N_4O_3{}^{35}Cl$ (M+H)$^+$, 337.1067. Found, 337.1015. calcd for $C_{15}H_{19}N_4O_3{}^{37}Cl$ (M+H)$^+$, 339.1038. Found, 339.0995.

Example 11

Synthesis of 1-((6-chloropyridin-3-yl)methyl)-2,3,5,6,7,8-hexahydro-1H-5,8-epoxyimidazo[1,2-a]azepine-9-carbonitrile (Compound 64)

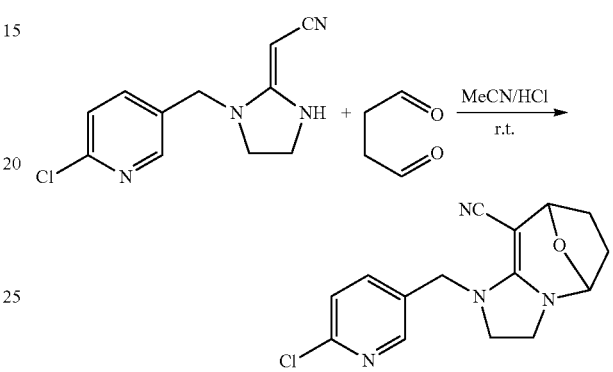

To a 50 ml round bottom flask was added 1.17 g (0.005 mol) 2-(1-((6-chloropyridin-3-yl)methyl)imidazolidin-2-ylidene)acetonitrile, 30 ml dry acetonitrile and 0.860 g (0.01 mol) succinaldehyde and catalytic concentrated HCl. The reaction was stirred at r.t. and monitored by TLC. After completion, the mixture was evaporated to remove solvent and purified by column chromatography to afford final product as faint yellow powder with 66% yield.

mp=125.1-126.8° C.; $^1$H NMR (400 Mz, DMSO-$d_6$): δ 8.34 (d, J=2.4 Hz, 1H), 7.82 (dd, $J_1$=2.4 Hz, $J_2$=8.4 Hz, 1H), 7.55 (d, J=8.4 Hz, 1H), 5.33 (s, 1H), 5.25 (s, 1H), 5.00 (d, J=15.6 Hz, 1H), 4.78 (d, J=15.6 Hz, 1H), 3.56-3.78 (m, 4H), 1.91-2.00 (m, 4H) ppm; $^{13}$C NMR (100 Mz, DMSO-$d_6$): δ 153.6, 149.0, 148.6, 139.7, 132.3, 121.5, 99.6, 87.3, 75.7, 51.3, 50.2, 46.6, 31.5, 29.7 ppm; HRMS (ES+) calcd for $C_{15}H_{16}N_4O^{35}Cl$ (M+H)$^+$, 303.1013. Found, 303.0992. calcd for $C_{15}H_{16}N_4O^{37}Cl$ (M+H)$^+$, 305.0983. Found, 305.0957.

Example 12

Synthesis of 1-((6-chloropyridin-3-yl)methyl)-10-nitro-1,2,3,5,6,7,8,9-octahydro-5,9-epoxyimidazo[1,2-a]azocine (Compound 77)

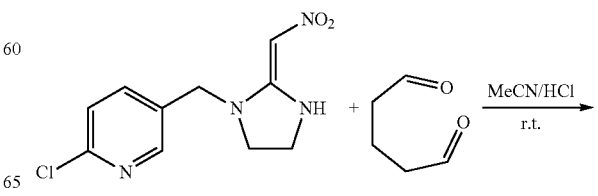

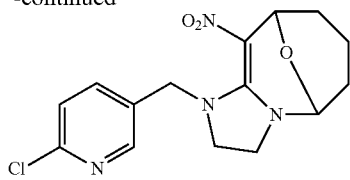

To a 50 ml round bottom flask was added 1.27 g (0.005 mol) 2-chloro-5-((2-(nitromethylene)imidazolidin-1-yl)methyl)pyridine, 30 ml acetonitrile, 3 ml 25% glutaraldehyde aqueous solution and catalytic concentrated HCl. The reaction was stirred at r.t. and monitored by TLC. After completion, the mixture was evaporated to remove solvent and purified by column chromatography to afford final product as faint yellow powder with 86% yield.

mp=174.7-175.4° C.; $^1$H NMR (400 Mz, DMSO-$d_6$): δ 8.38 (dd, $J_1$=0.6 Hz, $J_2$=2.4 Hz, 1H), 7.84 (dd, $J_1$=2.4 Hz, $J_2$=8.4 Hz, 1H), 7.52 (dd, $J_1$=0.6 Hz, $J_2$=8.4 Hz, 1H), 5.12 (s, 1H), 5.04-5.05 (m, 1H), 4.97 (d, J=15.6 Hz, 1H), 4.71 (d, J=15.6 Hz, 1H), 3.62-3.74 (m, 4H), 1.66-1.81 (m, 4H), 1.51-1.55 (m, 1H), 1.32-1.44 (m, 1H) ppm; $^{13}$C NMR (100 Mz, DMSO-$d_6$): δ 156.6, 149.7, 149.6, 139.7, 132.9, 124.5, 105.8, 81.7, 68.9, 51.7, 50.0, 46.3, 28.8, 27.2, 14.8 ppm; HRMS (EI+) calcd for $C_{15}H_{17}N_4O_3{}^{35}Cl$ ($M^+$), 336.0989. Found, 336.0988. calcd for $C_{15}H_{17}N_4O_3{}^{37}Cl$ ($M^{30}$), 338.0960. Found, 338.0968.

Example 13

Synthesis of 10-nitro-1-((tetrahydrofuran-3-yl)methyl)-1,2,3,5,6,7,8,9-octahydro-5,9-epoxyimidazo[1,2-a]azocine (Compound 80)

Following the method described in Example 1, 0.2 mol 3-(chloromethyl)tetrahydrofuran instead of 2-chloro-5-(chloromethyl)pyridine was used as staring material. 2-(nitromethylene)-1-((tetrahydrofuran-3-yl)methyl)imidazolidine was obtained with 51% yield. GC MS (m/s) 177(29), 99(100), 56 (9).

Synthesis of 10-nitro-1-((tetrahydrofuran-3-yl)methyl)-1,2,3,5,6,7,8,9-octahydro-5,9-epoxyimidazo[1,2-a]azocine

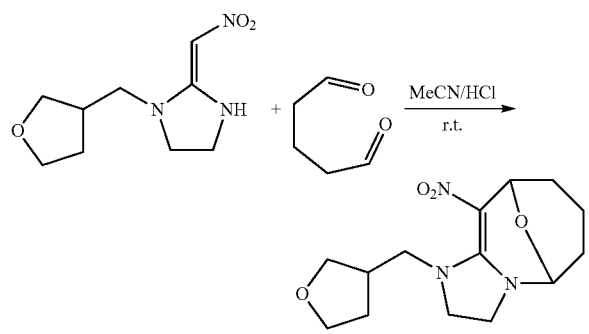

To a 50 ml round bottom flask was added 1.065 g (0.005 mol) 2-(nitromethylene)-1-((tetrahydrofuran-3-yl)methyl)imidazolidine, 30 ml acetonitrile, 3 ml 25% glutaraldehyde aqueous solution and catalytic concentrated HCl. The reaction was stirred at r.t. and monitored by TLC. After completion, the mixture was evaporated to remove solvent and purified by column chromatography to afford final product as yellow powder with 36% yield.

mp=115.3-116.9° C.; $^1$H NMR (400 Mz, DMSO-$d_6$): δ 5.11 (s, 1H), 5.00-5.03 (m, 1H), 4.18 (d, J=3.2 Hz, 2H), 4.05-4.25 (m, 2H), 3.85-3.96 (m, 4H), 2.25 (m, 1H), 1.66-1.81 (m, 4H), 1.63-1.64 (m, 2H), 1.57-1.59 (m, 2H), 1.51-1.55 (m, 1H), 1.32-1.44 (m, 1H) ppm; $^{13}$C NMR (100 Mz, DMSO-$d_6$): δ 81.7, 80.6, 78.5, 68.9, 50.0, 49.7, 46.9, 44.6, 36.8, 33.9, 28.8, 27.2, 17.8, 14.8 ppm; HRMS (EI+) calcd for $C_{14}H_{21}N_3O_4(M^+)$, 295.1532. Found, 295.1598.

Example 14

Insecticidal Activity Test of the Invented Compounds (1) Activity Test for Cowpea Aphids (*Aphis Craccivoral*)

Aphis, which belongs to Homoptera and has a piercing-sucking mouthpart, is a common insect for agricultural plant. *Aphis craccivoral* was tested by the way of immersing.

Test method: exactly weighed various samples were independently added to N,N-dimethylformamide to form a 10 g/L stock solution. The mixture was diluted with 0.2 mL/L aqueous Triton X-100 solution to a concentration of 500 ppm After stably sucking on bean sprout, the adult aphis without wings together with bean sprout was dipped into 500 ppm dilution, taken out after 5 seconds, and the excess dilution was sucked out with bibulous paper and the adult aphis without wings was incubated in clean vessel at a constant temperature of 23° C. Each concentration was repeated for 3 times and the control group contained 0.2 mL/L aqueous Triton X-100 solution. The number of killed aphas was counted after 24 hours to calculate the mortality by the following formula:

mortality(%)=(control alive aphis−treated alive aphis)/control alive aphis×100%.

The results were shown in Tables 1-4 bellow.

(2) Activity Test for Planthopper (*Nilaparvata lugens*)

Planthopper, which belongs to Homoptera and has a piercing-sucking mouthpart, is a common insect for agricultural plant. *Nilaparvata lugens* was tested by the way of spraying.

Test method: the test compound was exactly formulated into a solution of acetone to final concentration of 500, 250, 100, 50, 25, 12.5, 6.25, 3.13, 1.57 and 0.79 ppm. The acetone aqueous solution was used as control. Each process was repeated for 3 tumblers (3 times). 2 mL of solution was sprayed uniformly to each cup by a mini manual sprayer. 10 *Nilaparvata lugens* were introduced to every sink 6 hours before spraying. Three series of experiments were conducted. The number of killed *Nilaparvata lugens* was counted after 24 hours to calculate the mortality using above mentioned formula. The results were shown in Tables 1-4 bellow.

(3) Activity Test for Armyworm (*Pseudaletia Separate Walker*)

Armyworm was tested by the way of feeding immersed leaves. The test compound was exactly formulated into a solution of acetone to concentration 500, 250, 100, 50, 25, 12.5, 6.25, 3.13 and 1.57 ppm. The acetone aqueous solution was used as control. Fresh maize leaves were immersed in the solution for 3 seconds and dried at room temperature and used to feed the tested insects. Each process was repeated for 3 times while 10 Armyworms were tested in each experiment. The number of killed Armyworms was counted after 24 hours to calculate the mortality using above mentioned formula. The results were shown in Tables 1-4 bellow.

(4) Activity Test for Diamondback Moth (*Plutella Xylostella*)

Diamondback moth was tested by the way of feeding immersed leaves. Fresh cabbage leaves were immersed in above mentioned solution for 3 seconds and dried at room temperature and used to feed to the tested insects. Each process was repeated for 3 tumblers (3 times) while 10 Diamondback moths were tested in each experiment, while water was used as control. The number of killed Diamondback moth was counted after 24 hours to calculate the mortality using above mentioned formula. The results were shown in Tables 1-4 below.

TABLE 1

Insecticidal Activities of Compound of formula (A)

(A)

Structure: A compound with two $Y$ groups, an $OR_2$ group, $R_1CH_2N(R_3)$ and $N(R_4)H$ substituents on a diene/diimine backbone.

| Compd. No. | $R_1$ | $R_2$ | $R_3$ | $R_4$ | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|---|
| 1 | 6-Cl-pyridin-3-yl | H | $C_2H_5$ | $CH_3$ | $NO_2$ | 80 | 91 | 100 | 100 |
| 2 | 6-Cl-pyridin-3-yl | $CH_3$ | $C_2H_5$ | $CH_3$ | $NO_2$ | 100 | 100 | 100 | 100 |
| 3 | 6-Cl-pyridin-3-yl | $C_2H_5$ | $C_2H_5$ | $CH_3$ | $NO_2$ | 100 | 100 | 100 | 100 |
| 4 | 6-Cl-pyridin-3-yl | $C_3H_7$ | $C_2H_5$ | $CH_3$ | $NO_2$ | 100 | 100 | 100 | 100 |
| 5 | 6-Cl-pyridin-3-yl | $i\text{-}C_3H_7$ | $C_2H_5$ | $CH_3$ | $NO_2$ | 100 | 100 | 100 | 100 |
| 6 | 6-Cl-pyridin-3-yl | benzyl | $C_2H_5$ | $CH_3$ | $NO_2$ | 100 | 100 | 100 | 100 |
| 7 | 6-Cl-pyridin-3-yl | H | H | $CH_3$ | $NO_2$ | 24 | 35 | 35 | 21 |
| 8 | 6-Cl-pyridin-3-yl | $CH_3$ | H | $CH_3$ | $NO_2$ | 45 | 44 | 67 | 56 |
| 9 | 6-Cl-pyridin-3-yl | $C_2H_5$ | H | $CH_3$ | $NO_2$ | 89 | 87 | 100 | 100 |

TABLE 1-continued

Insecticidal Activities of Compound of formula (A)

$$\text{(A)}$$

Structure (A): a compound with R_2O- attached to a central carbon, flanked by two =C(Y)- groups each bearing -N(R_3)(CH_2R_1) and connected through -NH- / =N- linkages, with R_4 on the nitrogens.

| Compd. No. | R₁ | R₂ | R₃ | R₄ | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|---|
| 10 | 6-chloropyridin-3-yl | C₃H₇ | H | CH₃ | NO₂ | 45 | 36 | 87 | 90 |
| 11 | 6-chloropyridin-3-yl | i-C₃H₇ | H | CH₃ | NO₂ | 76 | 90 | 95 | 100 |
| 12 | 6-chloropyridin-3-yl | benzyl | H | CH₃ | NO₂ | 67 | 92 | 97 | 100 |
| 13 | 6-chloropyridin-3-yl | H | R₃ and R₄ together form —CH₂—CH₂— | | NO₂ | 78 | 85 | 100 | 100 |
| 14 | 6-chloropyridin-3-yl | CH₃ | R₃ and R₄ together form —CH₂—CH₂— | | NO₂ | 100 | 100 | 100 | 100 |
| 15 | 6-chloropyridin-3-yl | C₂H₅ | R₃ and R₄ together form —CH₂—CH₂— | | NO₂ | 100 | 100 | 100 | 100 |
| 16 | 6-chloropyridin-3-yl | C₃H₇ | R₃ and R₄ together form —CH₂—CH₂— | | NO₂ | 100 | 100 | 100 | 100 |
| 17 | 6-chloropyridin-3-yl | i-C₃H₇ | R₃ and R₄ together form —CH₂—CH₂— | | NO₂ | 100 | 100 | 100 | 100 |
| 18 | 6-chloropyridin-3-yl | benzyl | R₃ and R₄ together form —CH₂—CH₂— | | NO₂ | 100 | 100 | 100 | 100 |
| 19 | 6-chloropyridin-3-yl | H | R₃ and R₄ together form —CH₂—CH₂— | | CN | 90 | 100 | 100 | 100 |
| 20 | 6-chloropyridin-3-yl | H | R₃ and R₄ together form —CH₂—CH₂— | | CN | 98 | 100 | 100 | 100 |

TABLE 1-continued

Insecticidal Activities of Compound of formula (A)

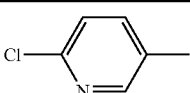

(A)

| Compd. No. | R₁ | R₂ | R₃ | R₄ | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|---|
| 21 | 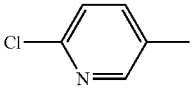 | H | R₃ and R₄ together form —CH₂—CH₂— | | CN | 100 | 100 | 100 | 100 |
| 22 | 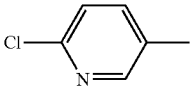 | H | R₃ and R₄ together form —CH₂—CH₂— | | CN | 73 | 100 | 92 | 100 |
| 23 | 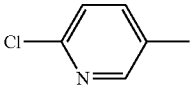 | H | R₃ and R₄ together form —CH₂—CH₂— | | CN | 56 | 87 | 87 | 100 |
| 24 | 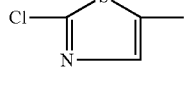 | H | R₃ and R₄ together form —CH₂—CH₂— | | CN | 65 | 83 | 90 | 100 |
| 25 | 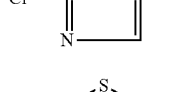 | H | R₃ and R₄ together form —CH₂—CH₂— | | NO₂ | 89 | 87 | 100 | 100 |
| 26 | 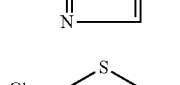 | H | R₃ and R₄ together form —CH₂—CH₂— | | NO₂ | 100 | 100 | 100 | 100 |
| 27 | 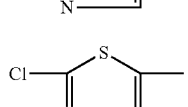 | H | R₃ and R₄ together form —CH₂—CH₂— | | NO₂ | 100 | 100 | 100 | 100 |
| 28 | 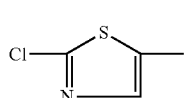 | H | R₃ and R₄ together form —CH₂—CH₂— | | NO₂ | 100 | 100 | 100 | 100 |
| 29 | 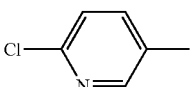 | H | R₃ and R₄ together form —CH₂—CH₂— | | NO₂ | 100 | 100 | 100 | 100 |
| 30 | 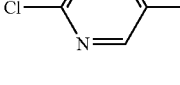 | H | R₃ and R₄ together form —CH₂—CH₂—CH₂ | | NO₂ | 100 | 100 | 100 | 100 |
| 31 |  | H | R₃ and R₄ together form —CH₂—CH₂—CH₂ | | NO₂ | 46 | 77 | 77 | 83 |

TABLE 1-continued

Insecticidal Activities of Compound of formula (A)

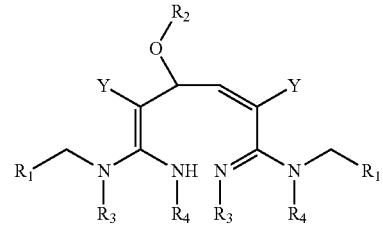

(A)

| Compd. No. | R₁ | R₂ | R₃ | R₄ | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|---|
| | | | | | | Insecticidal Activity | | | |
| 32 | 2-Cl-pyridin-5-yl-CH₂ | H | R₃ and R₄ together form —CH₂—CH₂—CH₂ | | NO₂ | 65 | 61 | 87 | 92 |
| 33 | 2-Cl-pyridin-5-yl-CH₂ | H | R₃ and R₄ together form —CH₂—CH₂—CH₂ | | NO₂ | 32 | 50 | 58 | 52 |
| 34 | 2-Cl-pyridin-5-yl-CH₂ | H | R₃ and R₄ together form —CH₂—CH₂—CH₂ | | NO₂ | 76 | 88 | 90 | 86 |
| 35 | 2-Cl-pyridin-5-yl-CH₂ | H | R₃ and R₄ together form —CH₂—CH₂—CH₂ | | NO₂ | 76 | 90 | 68 | 77 |
| 36 | 2-Cl-pyridin-5-yl-CH₂ | H | R₃ and R₄ together form —CH₂—CH₂—CH₂ | | NO₂ | 87 | 97 | 100 | 100 |

TABLE 2

Insecticidal Activities of Compound of formula (B)

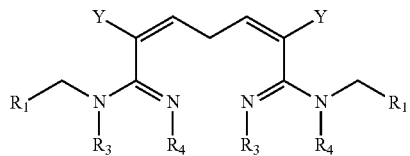

(B)

| Compd. No. | R₁ | R₃ | R₄ | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|
| | | | | | Insecticidal Activity | | | |
| 37 | 2-Cl-pyridin-5-yl-CH₂ | C₂H₅ | CH₃ | NO₂ | 100 | 100 | 100 | 100 |

TABLE 2-continued

| | | | | | | | | |
|---|---|---|---|---|---|---|---|---|
| 38 | 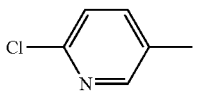 (6-chloropyridin-3-yl) | H | CH₃ | NO₂ | 100 | 100 | 100 | 100 |
| 39 | 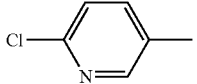 (6-chloropyridin-3-yl) | R₃ and R₄ together form —CH₂—CH₂— | | NO₂ | 100 | 100 | 100 | 100 |
| 40 | 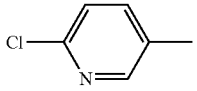 (6-chloropyridin-3-yl) | R₃ and R₄ together form —CH₂—CH₂— | | CN | 56 | 87 | 87 | 100 |
| 41 | 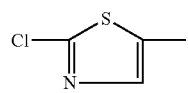 (2-chlorothiazol-5-yl) | R₃ and R₄ together form —CH₂—CH₂— | | NO₂ | 100 | 100 | 100 | 100 |
| 42 | 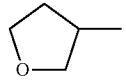 (tetrahydrofuran-3-yl) | R₃ and R₄ together form —CH₂—CH₂— | | NO₂ | 100 | 100 | 100 | 100 |
| 43 | 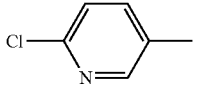 (6-chloropyridin-3-yl) | R₃ and R₄ together form —CH₂—CH₂— | | NO₂ | 78 | 87 | 100 | 96 |

TABLE 3

Insecticidal Activities of Compound of formula (C)

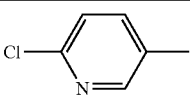

(C)

| | | | | | | | Insecticidal Activity | | | |
|---|---|---|---|---|---|---|---|---|---|---|
| | | | | | | | Cowpea Aphids Mortality (100%) 500 ppm | Planthopper Mortality (100%) 500 ppm | Armyworm Mortality (100%) 500 ppm | Diamondback moth Mortality (100%) 500 ppm |
| Compd. No. | R₁ | R₃ | R₄ | R₅ | R₆ | Y | | | | |
| 44 | 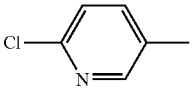 | H | CH₃ | H | H | NO₂ | 100 | 100 | 100 | 100 |
| 45 | 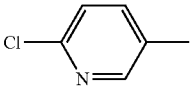 | CH₃ | CH₃ | H | H | NO₂ | 100 | 100 | 100 | 100 |
| 46 | 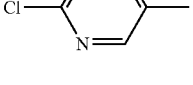 | C₂H₅ | CH₃ | H | H | NO₂ | 100 | 100 | 100 | 100 |
| 47 |  | H | H | H | H | NO₂ | 100 | 100 | 100 | 100 |

TABLE 3-continued

Insecticidal Activities of Compound of formula (C)

(C)

$$\text{Structure with } R_1, R_3, R_4, R_5, R_6, Y \text{ substituents}$$

| Compd. No. | $R_1$ | $R_3$ | $R_4$ | $R_5$ | $R_6$ | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|---|---|
| 48 | 2-Cl-pyridin-5-yl | $CH_3$ | H | H | H | $NO_2$ | 100 | 100 | 100 | 100 |
| 49 | 2-Cl-pyridin-5-yl | $C_2H_5$ | H | H | H | $NO_2$ | 100 | 100 | 100 | 100 |
| 50 | 2-Cl-pyridin-5-yl | $CH_3$ | $C_2H_5$ | H | H | $NO_2$ | 100 | 100 | 100 | 100 |
| 51 | 2-Cl-pyridin-5-yl | $C_2H_5$ | $C_2H_5$ | H | H | $NO_2$ | 100 | 100 | 100 | 100 |
| 52 | 2-Cl-pyridin-5-yl | $R_3$ and $R_4$ together form —$CH_2$—$CH_2$— | | H | H | $NO_2$ | 100 | 100 | 100 | 100 |
| 53 | 2-Cl-thiazol-5-yl | $R_3$ and $R_4$ together form —$CH_2$—$CH_2$— | | H | H | $NO_2$ | 100 | 100 | 100 | 100 |
| 54 | tetrahydrofuran-3-yl | $R_3$ and $R_4$ together form —$CH_2$—$CH_2$— | | H | H | $NO_2$ | 100 | 100 | 100 | 100 |
| 55 | 2-Cl-pyridin-5-yl | $R_3$ and $R_4$ together form —$CH_2$—$CH_2$— | | $CH_3$ | $CH_3$ | $NO_2$ | 100 | 100 | 100 | 100 |
| 56 | 2-Cl-thiazol-5-yl | $R_3$ and $R_4$ together form —$CH_2$—$CH_2$— | | $CH_3$ | $CH_3$ | $NO_2$ | 100 | 100 | 100 | 100 |
| 57 | tetrahydrofuran-3-yl | $R_3$ and $R_4$ together form —$CH_2$—$CH_2$— | | $CH_3$ | $CH_3$ | $NO_2$ | 100 | 100 | 100 | 100 |
| 58 | 2-Cl-pyridin-5-yl | $R_3$ and $R_4$ together form —$CH_2$—$CH_2$— | | F | F | $NO_2$ | 100 | 100 | 100 | 100 |

TABLE 3-continued

Insecticidal Activities of Compound of formula (C)

(C)

[Structure of formula (C): bicyclic compound with substituents R1-CH2-N(R3)-, N-R4, O bridge, R5, R6, and Y]

| Compd. No. | R1 | R3 | R4 | R5 | R6 | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|---|---|
| 59 | 2-Cl-thiazol-5-yl | | R3 and R4 together form —CH2—CH2— | F | F | NO2 | 100 | 100 | 100 | 100 |
| 60 | tetrahydrofuran-3-yl | | R3 and R4 together form —CH2—CH2— | F | F | NO2 | 100 | 100 | 100 | 100 |
| 61 | 6-Cl-pyridin-3-yl | | R3 and R4 together form —CH2—CH2—CH2— | H | H | NO2 | 65 | 75 | 76 | 35 |
| 62 | 2-Cl-thiazol-5-yl | | R3 and R4 together form —CH2—CH2—CH2— | H | H | NO2 | 75 | 50 | 89 | 33 |
| 63 | tetrahydrofuran-3-yl | | R3 and R4 together form —CH2—CH2—CH2— | H | H | NO2 | 37 | 76 | 53 | 87 |
| 64 | 6-Cl-pyridin-3-yl | | R3 and R4 together form —CH2—CH2— | H | H | CN | 96 | 56 | 100 | 100 |
| 65 | 2-Cl-thiazol-5-yl | | R3 and R4 together form —CH2—CH2— | H | H | CN | 80 | 86 | 98 | 100 |
| 66 | tetrahydrofuran-3-yl | | R3 and R4 together form —CH2—CH2— | H | H | CN | 37 | 44 | 50 | 41 |
| 67 | 6-Cl-pyridin-3-yl | | R3 and R4 together form —CH2—CH2— | H | CH3O | NO2 | 100 | 100 | 100 | 100 |
| 68 | 6-Cl-pyridin-3-yl | | R3 and R4 together form —CH2—CH2— | H | C2H5O | NO2 | 100 | 100 | 100 | 100 |
| 69 | 6-Cl-pyridin-3-yl | | R3 and R4 together form —CH2—CH2— | CH3O | H | NO2 | 100 | 100 | 100 | 100 |

TABLE 3-continued

Insecticidal Activities of Compound of formula (C)

(C) Structure: bicyclic with R$_5$, R$_6$, Y, R$_1$CH$_2$-N(R$_3$)-, N-R$_4$, O bridge.

| Compd. No. | R$_1$ | R$_3$ | R$_4$ | R$_5$ | R$_6$ | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|---|---|
| 70 | 6-Cl-pyridin-3-yl | | R$_3$ and R$_4$ together form —CH$_2$—CH$_2$— | C$_2$H$_5$O | H | NO$_2$ | 100 | 100 | 100 | 100 |
| 71 | 6-Cl-pyridin-3-yl | | R$_3$ and R$_4$ together form —CH$_2$—CH$_2$— | —C(O)H | H | NO$_2$ | 100 | 100 | 100 | 100 |
| 72 | 6-Cl-pyridin-3-yl | | R$_3$ and R$_4$ together form —CH$_2$—CH$_2$— | —C(O)CH$_3$ | H | NO$_2$ | 100 | 100 | 100 | 100 |
| 73 | 6-Cl-pyridin-3-yl | | R$_3$ and R$_4$ together form —CH$_2$—CH$_2$— | H | —C(O)H | NO$_2$ | 100 | 100 | 100 | 100 |
| 74 | 6-Cl-pyridin-3-yl | | R$_3$ and R$_4$ together form —CH$_2$—CH$_2$— | H | —C(O)CH$_3$ | NO$_2$ | 100 | 100 | 100 | 100 |

TABLE 4

Insecticidal Activities of Compound of formula (D)

(D) Structure: bicyclic with R$_7$, R$_8$, R$_9$, Y, R$_1$CH$_2$-N(R$_3$)-, N-R$_4$, O bridge.

| Compd. No. | R$_1$ | R$_3$ | R$_4$ | R$_7$, R$_8$, R$_9$ | Y | Cowpea Aphids Mortality (100%) 500 ppm | Planthopper Mortality (100%) 500 ppm | Armyworm Mortality (100%) 500 ppm | Diamondback moth Mortality (100%) 500 ppm |
|---|---|---|---|---|---|---|---|---|---|
| 75 | 6-Cl-pyridin-3-yl | C$_2$H$_5$ | CH$_3$ | H | NO$_2$ | 100 | 100 | 100 | 100 |

TABLE 4-continued

| 76 | Cl-pyridyl | H | CH₃ | H | NO₂ | 100 | 100 | 100 | 100 |
| 77 | Cl-pyridyl | R₃ and R₄ together form —CH₂—CH₂— | | H | NO₂ | 100 | 100 | 100 | 100 |
| 78 | Cl-pyridyl | R₃ and R₄ together form —CH₂—CH₂— | | H | CN | 56 | 87 | 87 | 100 |
| 79 | Cl-pyridyl | R₃ and R₄ together form —CH₂—CH₂— | | H | NO₂ | 100 | 100 | 100 | 100 |
| 80 | tetrahydrofuranyl | R₃ and R₄ together form —CH₂—CH₂— | | H | NO₂ | 100 | 100 | 100 | 100 |
| 81 | Cl-pyridyl | R₃ and R₄ together form —CH₂—CH₂—CH₂ | | H | NO₂ | 78 | 87 | 100 | 96 |

Example 15

Preparation of Insecticidal Composition Containing the Invented Active Compound (a) Oily Suspension The following components were prepared: 25 wt % of any compound selected from compounds 1-73; 5 wt % polyoxyethylene sorbital hexaoleate and 70 wt % higher aliphatic hydrocarbon oil. All of the components were ground in a sand mill until the solid granules were reduced to less than about 5 micrometer. The resultant viscous suspension could be used directly or may be used after it was emulsified in water.

(b) Aqueous Suspension

The following components were prepared: 25 wt % of any compound selected from compounds 1-73; 3 wt % hydrate attapulagit; 10 wt % calcium lignosulphonate; 0.5 wt % sodium dihydrogen phosphate and 61.5 wt % water. All of the components were ground in a ball mill until the solid granules were reduced to less than about 10 micrometer. The aqueous suspension could be used directly.

(c) Bait Formulation

The following components were prepared: 0.1-10 wt % of any compound selected from compounds 1-73; 80 wt % wheat flour and 19.9-10 wt % molasses. All of the components were sufficiently mixed and shaped according to the need. The edible bait could be oral ingested or distributed to domestic or industrial places such as kitchen, hospital, store and outdoor area infected by public health insects.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be within the scope of the invention defined by the appended claims of the application.

What is claimed is:

1. A compound of formula (C) or (D), its optical isomer, cis-trans isomer, or its agrochemically acceptable salts thereof,

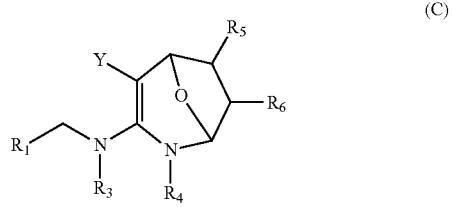

(C)

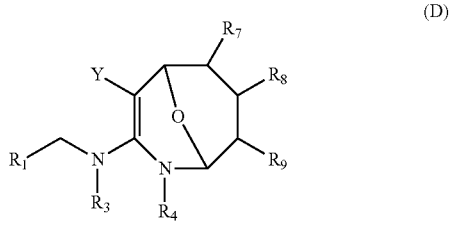

(D)

wherein $R_1$ is 5 or 6 membered heterocycle containing nitrogen, oxygen and/or sulfur atom, halo-substituted 5 or 6 membered heterocycle containing nitrogen, oxygen and/or sulfur atom, substituted or unsubstituted phenyl, wherein the substituents are one or more groups selected from the group consisting of halogen atoms, $C_{1-4}$ haloalkyl or $C_{1-4}$ chloro-alkoxyl;

$R_3$ and $R_4$ are independently selected from H, $C_{1-6}$ alkyl, allyl, benzyl, $C_{1-4}$ alkoxyl-$C_{1-4}$ alkyl, $C_{1-4}$ alkoxyl-carbonyl, phenoxycarbonyl, $C_{2-6}$ alkynyl-carbonyl, $C_{2-3}$ alkenyl-carbonyl, $C_{3-6}$ cycloalkyl-carbonyl, unsubstitued benzoyl group or benzoyl group substituted by one or more groups selected from the group consisting of halogen atoms, $C_{1-4}$ alkyl, $C_{1-4}$ halo-alkyl, $C_{1-4}$ alkoxyl or $C_{1-4}$ alkyl-carbonyl, furan carbonyl or N,N-dimethyl carbonyl; or $R_3$ and $R_4$ together form —CH₂—

$CH_2$—, —$CH_2$—$CH_2$—$CH_2$— or —$CH_2$—XR—$CH_2$—, wherein X represents-heteroatom; R is substituent on X and selected from H, $C_{1-6}$ alkyl, allyl, benzyl, phenyl, $C_{1-4}$ alkoxyl-$C_{1-4}$ alkyl, $C_{1-4}$ alkoxyl-carbonyl, phenoxycarbonyl, $C_{2-6}$ alkynyl-carbonyl, $C_{2-3}$ alkenyl-carbonyl, $C_{3-6}$ cycloalkyl-carbonyl, unsubstitued benzoyl group or benzoyl group substituted by one or more groups selected from the group consisting of halogen atoms, $C_{1-4}$ halo-alkyl, $C_{1-8}$ saturated or unsaturated alkyl or alkoxyl, or $C_{1-4}$ alkyl-carbonyl, furan carbonyl or N,N-dimethyl carbonyl, $R_5$, $R_6$, $R_7$, $R_8$ and $R_9$ are H, saturated or unsaturated $C_{1-4}$ alkyl, halogen, saturated or unsaturated $C_{1-8}$ alkoxyl, saturated or unsaturated $C_{1-4}$ halo-alkoxyl, $C_{1-4}$ alkyl-carbonyl, $C_{1-8}$ alkyl-ester, $C_{1-4}$ alkyl-sulfonyl, phenyl or benzyl;

Y is nitro, cyano, trifluoromethyl, trifluoroacetyl, or trifluoromethylsulfonyl.

2. The compound, its optical isomer or cis-trans isomer, or its agrochemically acceptable salts of claim 1 wherein $R_1$ is selected from pyridyl, thiazolyl, pyrimidinyl, tetrahydrofuryl, oxazolyl, or the halogenated groups thereof.

3. The compound, its optical isomer or cis-trans isomer, or its agrochemically acceptable salts of claim 1, wherein $R_3$ and $R_4$ are H, $C_{1-6}$ alkyl group, or $R_3$ and $R_4$ together form —$CH_2$—$CH_2$— or —$CH_2$—$CH_2$—$CH_2$—.

4. The compound, its optical isomer or cis-trans isomer, or its agrochemically acceptable salts of claim 1 wherein $R_5$, $R_6$, $R_7$, $R_8$ and $R_9$ are H, saturated or unsaturated $C_{1-2}$ alkyl, halogen, saturated or unsaturated $C_{1-4}$ alkoxyl, saturated or unsaturated $C_{1-2}$ halo-alkoxyl, $C_{1-4}$ alkyl-ester group (RCOO—), $C_{1-2}$ alkyl-sulfonyl or trifluoromethanesulfonyl ester group.

5. The compound, its optical isomer or cis-trans isomer, or its agrochemically acceptable salts of claim 1 wherein Y is nitro group or cyano group.

6. An agrochemical composition comprising:
(a) 0.001-99.99 wt % of the compound, its optical isomer, cis-trans isomer, agrochemically acceptable salts thereof according to claim 1; and
(b) an agrochemically acceptable carrier or excipient.

7. A method of killing or controlling agricultural pests, sanitary pests and animal health hazard pests, wherein the method comprises applying the agrochemical composition according to claim 6 onto plans or surrounding soil thereof.

8. A method for preparation of the compound, its optical isomer or cis-trans isomer, or an agrochemically acceptable salts according to claim 1, wherein the method comprises the following steps:

in the presence of catalytic acid and at 0-60° C., reacting compound of formula (a) with compound (c) or (d), thereby forming compound (C) or (D),

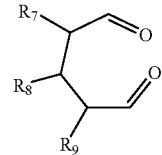

(a)

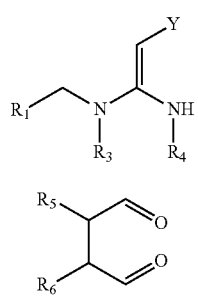

(c)

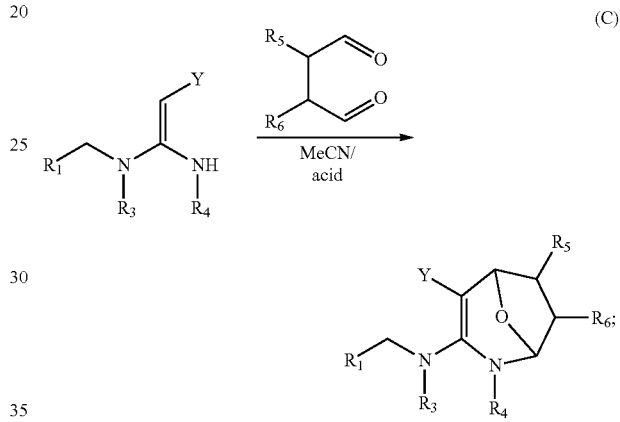

(d)

wherein $R_1$, $R_3$, $R_4$, $R_5$, $R_6$, $R_7$, $R_8$, $R_9$ and Y are defined as in claim 1.

9. The method of claim 8 wherein the method comprises:

in the presence of catalytic acid, the following reaction is carried out at 10-50° C. in acetonitrile for 2-24 hours, thereby forming compound (C):

(C)

in the presence of catalytic acid, the following reaction is carried out at 10-50° C. in acetonitrile for 2-24 hours, thereby forming compound (D):

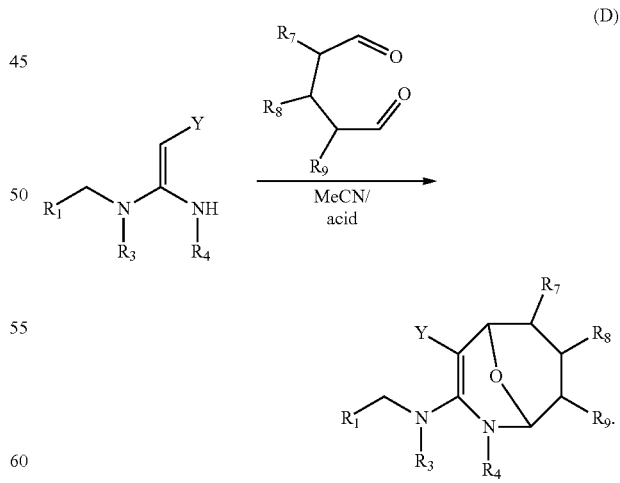

(D)

* * * * *